(12) United States Patent
Cai et al.

(10) Patent No.: US 10,144,713 B1
(45) Date of Patent: Dec. 4, 2018

(54) BIS-CYCLIC GUANIDINES AS ANTIBACTERIAL AGENTS

(71) Applicant: UNIVERSITY OF SOUTH FLORIDA, Tampa, FL (US)

(72) Inventors: Jianfeng Cai, Tampa, FL (US); Peng Teng, Tampa, FL (US); Alekhya Nimmagadda, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/014,702

(22) Filed: Jun. 21, 2018

Related U.S. Application Data

(60) Provisional application No. 62/536,295, filed on Jul. 24, 2017.

(51) Int. Cl.
| | |
|---|---|
| C07D 233/46 | (2006.01) |
| A61P 31/04 | (2006.01) |
| A61K 31/4178 | (2006.01) |
| A61K 45/06 | (2006.01) |

(52) U.S. Cl.
CPC ........ *C07D 233/46* (2013.01); *A61K 31/4178* (2013.01); *A61K 45/06* (2013.01); *A61P 31/04* (2018.01)

(58) Field of Classification Search
None
See application file for complete search history.

(56) References Cited

U.S. PATENT DOCUMENTS 7,211,669 B2    5/2007 Vrudhula et al.

FOREIGN PATENT DOCUMENTS

| CN | 102627600 | * | 8/2012 |
|---|---|---|---|
| WO | 2015/130547 A1 | | 9/2015 |

OTHER PUBLICATIONS

Andes et al., "In Vivo Pharmacodynamics of a New Oxazolidinone (Linezolid)," Antimicrob. Agents Chemother, 2002, 46, 3484-3489.
Bjarnsholt et al., "Applying insights from biofilm biology to drug development—can a new approach be developed?," Nat. Rev. Drug. Discov, 2013, 12, 791-808.
Bottcher et al., "Synthesis and activity of biomimetic biofilm disruptors," J. Am. Chem. Soc., 2013, 135, 2927-30.
Brauner et al., "Distinguishing between resistance, tolerance and persistence to antibiotic treatment," Nat. Rev. Microbiol., 2016, 14, 320-30.
Bremner et al., "Binaphthyl-based dicationic peptoids with therapeutic potential," Angew. Chem., Int. Ed., 2010, 49, 537-40.
Brown et al., "Cationic host defense (antimicrobial) peptides," Current Opinion in Immunology, 2006, 18, 24-30.
Bush et al., "Tackling antibiotic resistance," Nat. Rev. Microbiol., 2011, 9, 894-6.
C.T.F.A. Cosmetic Ingredient Handbook, 1992, pp. 587-592.
Choi et al., "De novo design and in vivo activity of conformationally restrained antimicrobial arylamide foldamers," Proc. Natl. Acad. Sci. U. S. A., 2009, 106, 6968-6973.
Davies, "Understanding biofilm resistance to antibacterial agents," Nat. Rev. Drug. Discov, 2003, 2, 114-22.
Doyle et al., "Antimicrobial Resistance: Challenges and Perspectives," Compr. Rev. Food Sci. Food Saf., 2013, 12, 234-248.
Fernandez-Lopez et al., "Antibacterial agents based on the cyclic d,l-[alpha]-peptide architecture," Nature, 2001, 412, 452-455.
Fleeman et al., "Combinatorial Libraries as a Tool for the Discovery of Novel, Broad-Spectrum Antibacterial Agents Targeting the ESKAPE Pathogens," J. Med. Chem. 2015, 58, 3340-55.
Flemming et al., "Biofilms: an emergent form of bacterial life," Nature Rev. Microbiol., 2016, 14, 563-575.
Ghosh et al., "Small molecular antibacterial peptoid mimics: the simpler the better!," J. Med. Chem., 2014, 57, 1428-36.
Grare et al., "Cationic compounds with activity against multidrug-resistant bacteria: interest of a new compound compared with two older antiseptics, hexamidine and chlorhexidine," Clin. Microbiol. Infect., 2010, 16, 432-438.
Guchhait et al., "Amphiphilic tobramycins with immunomodulatory properties," Angew. Chem., Int. Ed. 2015, 54, 6278-82.
Hancock et al., "Antimicrobial and host-defense peptides as new anti-infective therapeutic strategies," Nat Biotechnol, 2006, 24, 1551-7.
Hancock et al., "Host defence peptides from invertebrates—emerging antimicrobial strategies," Immunobiology, 2006, 211, 315-322.
Robley et al., "Norspermidine is Not a Self-Produced Trigger for Biofilm Disassembly," Cell, 2014, 156, 844-854.
Koh et al., "Amino acid modified xanthone derivatives: novel, highly promising membrane-active antimicrobials for multidrug-resistant Gram-positive bacterial infections," J. Med. Chem., 2015, 58, 739-52.
Kowalski et al., "An Independent Evaluation of a Novel Peptide Mimetic, Brilacidin (PMX30063), for Ocular Anti-infective," J. Ocul. Pharmacol. Ther., 2016, 32, 23-7.
Leikin et al., "Chlorhexidine Gluconate", Poisoning and Toxicology Handbook (4th ed.) Informa, 2008, 183-184.
Levy et al., "Antibacterial resistance worldwide: causes, challenges and responses," Nat. Med., 2004, S122-129.
Li et al., "Helical Antimicrobial Sulfono-gamma-Aapeptides," J. Med. Chem., 2015, 58, 4802-4811.
Lin et al., "Symmetrically Substituted Xanthone Amphiphiles Combat Gram-Positive Bacterial Resistance with Enhanced Membrane Selectivity," J. Med. Chem., 2017, 60, 1362-1378.
Ling et al., "A new antibiotic kills pathogens without detectable resistance," Nature 2015, 517, 455-9.
Marr et al., "Antibacterial peptides for therapeutic use: obstacles and realistic outlook," Curr. Opin. Pharmacol., 2006, 6, 468-72.

(Continued)

*Primary Examiner* — Kamal A Saeed
(74) *Attorney, Agent, or Firm* — Michael Best & Friedrich LLP

(57) ABSTRACT

Provided are novel bis-cyclic guanidine compounds, and the use thereof for treating bacterial infection.

20 Claims, 5 Drawing Sheets
(5 of 5 Drawing Sheet(s) Filed in Color)

(56) References Cited

OTHER PUBLICATIONS

Matsuzaki, "Control of cell selectivity of antimicrobial peptides. Biochimi. Biophys," ACTA Biomembr., 2009, 1788, 1687-1692.
McCutcheon's vol. 1, Emulsifiers & Detergents, 1994, North American Edition, pp. 236-239.
Mensa et al., "Antibacterial Mechanism of Action of Arylamide Foldamers," Antimicrob. Agents Chemother., 2011, 55, 5043-5053.
Mercer et al., "Peptides as the next generation of anti-infectives," Future Medicinal Chemistry, 2013, 5, 315-337.
Niu et al., "Identification of gamma-AApeptides with potent and broad-spectrum antimicrobial activity," Chem Commun (Camb), 2011, 47, 12197-12199.
Niu et al., "Lipo-gamma-AApeptides as a new class of potent and broad-spectrum antimicrobial agents," J Med Chem 2012, 55, 4003-4009.
Niu et al., "Recent development of small antimicrobial peptidomimetics," Future Med. Chem., 2012, 4, 1853-1862.
O'Connell et al., "Combating multidrug-resistant bacteria: current strategies for the discovery of novel antibacterials," Angew. Chem., Int. Ed., 2013, 52, 10706-33.
O'Daniel et al., "Discovery of a new class of non-beta-lactam inhibitors of penicillin-binding proteins with Gram-positive antibacterial activity," J. Am. Chem. Soc., 2014, 136, 3664-72.
Padhee et al., "Activity of lipo-cyclic gamma-AApeptides against biofilms of *Staphylococcus epidermidis* and Pseudomonas aeruginosa," Bioorg. Med. Chem. Lett., 2015, 25, 2565-9.
Park et al., "Discovery of cahuitamycins as biofilm inhibitors derived from a convergent biosynthetic pathway," Nat. Commun., 2016, 7, 10710.
Radzishevsky et al., "Improved antimicrobial peptides based on acyl-lysine oligomers," Nat. Biotech., 2007, 25, 657-659.
Raulji et al., "Daily Bathing with Chlorhexidine and Its Effects on Nosocomial Infection Rates in Pediatric Oncology Patients," J. Pediatr. Hematol. Oncol., 2015, 32, 315-321.
Remington's Pharmaceutical Sciences, 15th Ed. 1975, pp. 335-337.
Sengupta et al., "Toroidal pores formed by antimicrobial peptides show significant disorder," Biochim. Biophys. Acta., 2008, 1778, 2308-17.
Teng et al., "Small Antimicrobial Agents Based on Acylated Reduced Amide Scaffold," J. Med. Chem., 2016, 59, 7877-7887.
Tew et al., De Novo Design of Antimicrobial Polymers, Foldamers, and Small Molecules: From Discovery to Practical Applications. Acc. Chem. Res., 2010, 43, 30-39.
Vallon-Eberhard et al., "Efficient Clearance of Aspergillus fumigatus in Murine Lungs by an Ultrashort Antimicrobial Lipopeptide, Palmitoyl-Lys-Ala-dAla-Lys," Antimicrob. Agents Chemother., 2008, 52, 3118-3126.
Wang et al., "Antibacterial Diamines Targeting Bacterial Membranes," J. Med. Chem., 2016, 59, 3140-51.
Weis et al., "Daptomycin, a lipopeptide antibiotic in clinical practice," Curr Opin Investig Drugs, 2008, 9, 879-84.
WHO. Antimicrobial resistance: global report on surveillance. 2014.
Wu et al., "Design and synthesis of unprecedented cyclic gamma-AApeptides for antimicrobial development," Chem. Sci., 2012, 3 2570-2575.
Yahav et al., "Colistin: new lessons on an old antibiotic," Clinical Microbiology and Infection, 2012, 18, 18-29.
Yoganathan et al., "Structure diversification of vancomycin through peptide-catalyzed, site-selective lipidation: a catalysis-based approach to combat glycopeptide-resistant pathogens," J. Med. Chem., 2015, 58, 2367-77.
Zheng et al., "Enterobactin-mediated delivery of beta-lactam antibiotics enhances antibacterial activity against pathogenic *Escherichia coli*," J. Am. Chem. Soc., 2014, 136, 9677-91.
Hensler et al., "Pyrrolidine bis-cyclic guanidines with antimicrobial activity against drug-resistant Gram-positive pathogens identified from a mixture-based combinatorial library," Bioorganic & Medicinal Chemistry Letters, 2006, 16(19): 5073-9.
Rideout et al., "Potent antimicrobial small molecules screened as inhibitors of tyrosine recombinases and Holliday junction-resolving enzymes," Mol Divers, 2011, 15: 989-1005.
International Search Report and Written Opinion for Application No. PCT/US2018/038716 dated Sep. 25, 2018 (11 pages).

\* cited by examiner

Compound 11

Compound 12

BIS-CYCLIC GUANIDINES AS ANTIBACTERIAL AGENTS

CROSS-REFERENCE TO RELATED APPLICATION(S)

This application claims the benefit of and priority to U.S. Provisional Patent Application No. 62/536,295, filed on Jul. 24, 2017, the entire content of which is fully incorporated herein by reference.

STATEMENT OF GOVERNMENT SUPPORT

This invention was made with government support under Grant Number 1351265 awarded by the National Science Foundation, and Grant Number GM112652 awarded by the National Institutes of Health. The government has certain rights in the invention.

FIELD

Provided are novel bis-cyclic guanidine compounds and their use as antibacterial agents.

INTRODUCTION

Antimicrobial resistance is an escalating threat in global public health, and requires consistent actions worldwide. Indeed, multidrug-resistant bacterial strains, including Gram-positive bacteria methicillin-resistant *Staphylococcus aureus* (MRSA), methicillin-resistant *Staphylococcus epidermidis* (MRSE), Vancomycin-Resistant Enterococci (VRE), and Gram-negative bacteria *Escherichia coli* (*E. Coli*), *Klebsiella pneumoniae* (KP), and *Pseudomonas aeruginosa* (PA), have emerged to be the major cause of hospital and community-acquired infections. Compared with non-resistant infections, these multidrug-resistant infections have led to much heavier health care cost and increased risk of worse clinical outcomes including even death. To this end, significant efforts have been devoted to combating the abovementioned notorious bacterial strains.

Bis-guanidine related compounds such as hexamidine have been used as antiseptics and disinfectants in past decades (Raulji et al., *J. Pediatr. Hematol. Oncol.* 2015, 32, 315-321; Grare et al., *Clin. Microbiol. Infect.* 2010, 16, 432-438). Norspermidine analogues were reported as biomimetic biofilm disruptors with increased potency in preventing biofilm formation and breaking down existing biofilms, but with low potency in bactericidal test (Bottcher et al., *J. Am. Chem. Soc.* 2013, 135, 2927-30; Hobley et al., *Cell* 2014, 156, 844-854). A series of bis-cyclic guanidine compounds were recently obtained from combinatorial libraries and showed broad-spectrum antibacterial activity, however, the structures of these compounds lack symmetry and rational design, and thus could face challenge in further optimization (Fleeman et al., *J. Med. Chem.* 2015, 58, 3340-55). Amphipathic xanthone derivatives bearing bis-arginine moieties recently demonstrated enhanced membrane selectivity, although they showed potent antimicrobial activity only against Gram-positive bacteria including MRSA and VER (Lin et al., *J. Med. Chem.* 2017, 60, 1362-1378; Koh et al., *J. Med Chem.* 2015, 58, 739-52). Brilacidin, a symmetric bis-guanidine investigational new drug candidate also designed to mimic the mechanism of action of host-defense peptides (HDPs), possesses an amphipathic structure to replicate the innate function of HDPs (Kowalski et al., *J. Ocul. Pharmacol. Ther.* 2016, 32, 23-7).

Nevertheless, there remains a great need for new classes of antibiotic agents that have broad-spectrum antimicrobial activities, especially those with high efficacy to inhibit a panel of bacteria without developing drug-resistance.

SUMMARY

In one aspect, provided are compounds of formula (I), or a salt thereof

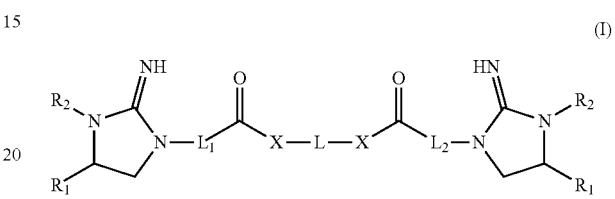

(I)

wherein
$R_1$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;
$R_2$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;
X is O or NH
$L_1$ is —$(CR_xR_y)_{n1}$—;
$L_2$ is —$(CR_xR_y)_{n2}$—;
L is —$(CR_xR_y)_{n3}$—$(CH_2CH_2O)_{m1}$-G-$(CH_2CH_2O)_{m2}$—$(CR_xR_y)_{n4}$—
$R_x$ and $R_y$ at each occurrence is independently hydrogen or $C_1$-$C_4$ alkyl;
G is a bond or -$(G_1)_t$-, wherein $G_1$ at each occurrence is independently aryl, cycloakyl, heteroaryl, or heterocycle;
n1 and n2 are each independently 1-4;
m1, m2, n3, and n4 are each independently 0-10;
t is 1, 2, 3, or 4; and
wherein $R_1$, $R_2$, $R_x$, $R_y$, and $G_1$ optionally are each independently substituted with one or more substituents selected from the group consisting of halogen, cyano, —OH, $C_1$-$C_6$ alkoxy, —COOH, $C_1$-$C_6$ alkoxycarbonyl, oxo, and amino.

In another aspect, provided are methods of inhibiting infection, including biofilm infection and infection caused by drug-resistant bacteria, in a subject in need thereof, the method comprising administering to the subject an effective amount of a compound of formula (I).

Other aspects of the invention will become apparent by consideration of the detailed description and accompanying drawings.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 shows the fluorescence micrographs of *S. aureus* (FIG. 1A) and *E. coli* (FIG. 1B) that were treated or not treated with 10 μg/mL of compound 12 for 2 h: a1, control, no treatment, DAPI stained; a2, control, no treatment, PI stained; a3, treatment with 12, DAPI stained; a4, treatment with compound 12, PI stained. Scale bar=10 m.

Figure 2A:
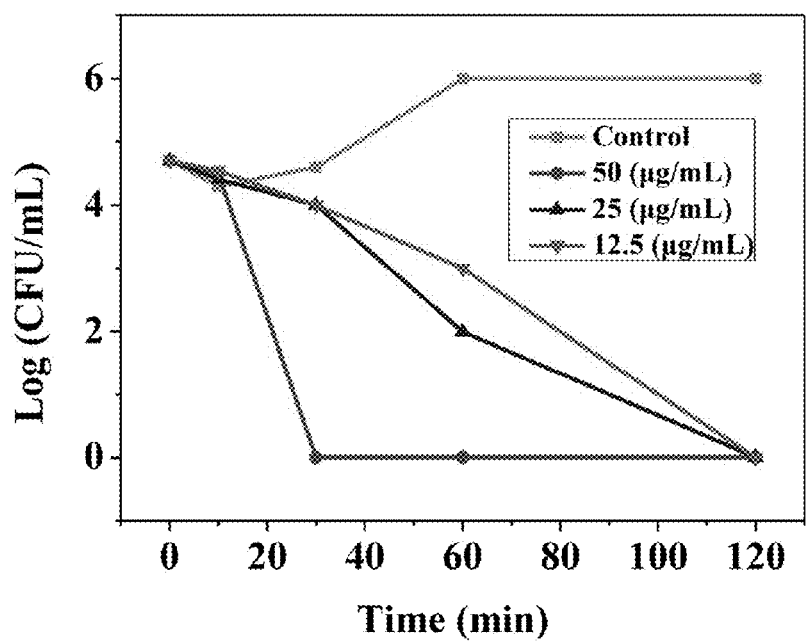
FIG. 2 shows the time-kill curves of compounds 11 (FIG. 2A) and 12 (FIG. 2B) for *E. Coli*. The killing activity was monitored for the first 2 h. The concentrations for compound 11 were 2×MIC, 4×MIC, and 8×MIC, respectively. The concentrations for compound 12 were 4×MIC, 8×MIC, and 16×MIC, respectively.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

DETAILED DESCRIPTION

Disclosed herein are novel bis-cyclic guanidine compounds and compositions thereof. Also disclosed herein are methods of treating infection, such as bacterial infections, using these compounds.

1. Definitions

The use of "including," "comprising," or "having" and variations thereof herein is meant to encompass the items listed thereafter and equivalents thereof as well as additional items. Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Definitions of specific functional groups and chemical terms are described in more detail below. For purposes of this disclosure, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

As used herein, the term "alkyl" refers to a linear or branched hydrocarbon radical, preferably having 1 to 30 carbon atoms, 1 to 10 carbon atoms, 1 to 6 carbon atoms or 1 to 4 carbon atoms. The term "$C_1$-$C_4$ alkyl" is defined to include alkyl groups having 1, 2, 3, or 4 carbons in a linear or branched arrangement. For example, "$C_1$-$C_4$ alkyl" specifically includes methyl, ethyl, n-propyl, i-propyl, n-butyl, t-butyl, and i-butyl. The term "$C_1$-$C_6$ alkyl" is defined to include alkyl groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl and hexyl.

As used herein, the term "arylalkyl" refers to an aryl group, as defined herein, appended to the parent molecular moiety through an alkyl group, as defined herein. In some embodiments, the alkyl group is $C_1$-$C_4$ alkyl or $C_1$-$C_6$ alkyl. In some embodiments, the arylalkyl group is an aryl-$C_1$-$C_6$ alkyl group.

As used herein, the term "alkynyl" refers to a straight or branched hydrocarbon radical having 2, 3, 4, 5, 6, 7, 8, 9 or 10 carbons and having one or more carbon-carbon triple bonds. Alkynyl groups of the present invention include, but are not limited to, ethynyl, propynyl and butynyl. Alkynyl groups of the present invention may be unsubstituted or substituted by one or more suitable substituents, preferably 1 to 3 suitable substituents, as defined above.

As used herein, the term "amino" refers to an —NH$_2$ group, optionally substituted with one or two $C_1$-$C_{10}$ alkyl groups.

As used herein, the term "aryl" refers to monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl.

As used herein, the term "carbonyl" or "(C═O)" (as used in phrases such as alkylcarbonyl, alkyl —(C═O)— or alkoxycarbonyl) refers to the joinder of the >C═O moiety to a second moiety such as an alkyl or amino group (i.e. an amido group). Alkoxycarbonylamino (i.e. alkoxyl (C═O)—NH—) refers to an alkyl carbamate group. The carbonyl group is also equivalently defined herein as (C═O). Alkylcarbonylamino refers to groups such as acetamide.

As used herein, the term "carboxylic acid" refers to COOH.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds.

As used herein, the term "halogen" or "halo" refers to a fluoro, chloro, bromo or iodo radical.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.13,7]decane. Heterocyclic groups of the present invention may contain one or more oxo groups (═O) or thioxo (═S) groups attached to the ring.

As used herein, the term "hydroxyl" refers to an —OH group.

As used herein, the term "oxo" refers to a double bonded oxygen (═O) radical wherein the bond partner is a carbon atom. Such a radical can also be thought as a carbonyl group.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 nonhydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 nonhydrogen radical.

As used herein, "treat", "treatment", "treating", and the like refer to acting upon a condition with an agent to affect the condition by improving or altering it. The condition includes, but is not limited to infection, such as those caused by bacteria. For example, the condition may include drug resistant bacterial biofilm infection caused by MRSA. The agent includes, but is not limited to, compounds capable of inhibiting or preventing infection, such as those caused by bacteria. For example, the agent may include a bis-cyclic guanidine compound described herein. The improvement or alteration may include an improvement in symptoms or an alteration in the physiologic pathways associated with the condition. The aforementioned terms cover one or more treatments of a condition in a subject (e.g., a mammal, typically a human or non-human animal of veterinary interest), and include: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reducing or eliminating the infection).

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used herein includes one or more such excipients, diluents, carriers, and adjuvants.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like. The subject may be immuno-compromised. The subject may be immunosuppressed.

The "therapeutically effective amount" for purposes herein may be determined by such considerations as are known in the art. A therapeutically effective amount of an agent (such as a bis-cyclic guanidine compound disclosed herein) may include the amount necessary to provide a therapeutically effective result in vivo. The amount of the compounds must be effective to achieve a response, including but not limited to a total prevention of (e.g., protection against) of a condition, improved survival rate or more rapid recovery, improvement or elimination of symptoms associated with the condition (such as drug resistant biofilm infection caused by MRSA), or other indicators as are selected as appropriate measures by those skilled in the art.

As used herein, a suitable single dose size includes a dose that is capable of preventing or alleviating (reducing or eliminating) a symptom in a subject when administered one or more times over a suitable time period. The "therapeutically effective amount" of a compound as described herein may depend on the route of administration, type of subject being treated, and the physical characteristics of the subject. These factors and their relationship to dose are well known to one of skill in the medicinal art, unless otherwise indicated.

As used herein, the term "$IC_{50}$" quantifies the ability of a compound to inhibit a specific biological or biochemical function. The $IC_{50}$ may refer to the concentration of a compound that kills 50% of bacterial cells. The $IC_{50}$ may refer to the concentration of a compound that inhibits biofilm formation by 50%.

As used herein, the term "MIC" or "minimum inhibitory concentration" means the minimum concentration of including, but not limited to, an antibiotic, drug, agent, chemical, compound, or composition, that prevents visible growth of bacteria.

The terms "administration" or "administering" as used herein may include the process in which the agents or compounds as described herein, alone or in combination with other agents or compounds, are delivered to a subject. The composition may be administered in various routes including, but not limited to, oral, parenteral (including intravenous, intra-arterial, and other appropriate parenteral routes), intrathecally, intramuscularly, subcutaneously, colonically, rectally, and nasally, transcutaneously, among others. Each of these conditions may be readily treated using other administration routes of compounds of the present invention. The dosing of the agents, compounds, and compositions described herein to obtain a therapeutic or prophylactic effect may be determined by the circumstances of the subject, as known in the art. The dosing of a subject herein may be accomplished through individual or unit doses of the compounds or compositions herein or by a combined or prepackaged or pre-formulated dose of a compounds or compositions.

Administration may depend upon the amount of compound administered, the number of doses, and duration of treatment. For example, multiple doses of the agent may be administered. The frequency of administration of the compound may vary depending on any of a variety of factors, such as extent of anxiety-related behavior, and the like. The duration of administration of the compound, e.g., the period of time over which the compound is administered, may vary, depending on any of a variety of factors, including subject response, etc.

The amount of the agent or compound contacted (e.g., administered) may vary according to factors such as the degree of susceptibility of the individual, the age, sex, and weight of the individual, idiosyncratic responses of the individual, the dosimetry, and the like. Detectably effective amounts of the agent or compound of the present disclosure may also vary.

2. Compound

In one aspect, disclosed are bis-cyclic guanidine compounds having the structure of formula (I), or a salt thereof

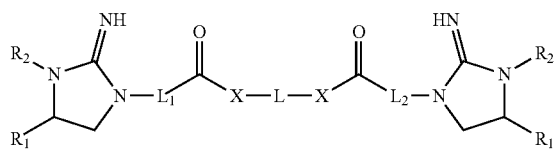

(I)

wherein $R_1$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;

$R_2$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;

X is O or NH $L_1$ is —$(CR_xR_y)_{n1}$;

$L_2$ is —$(CR_xR_y)_{n2}$;

L is —$(CR_xR_y)_{n3}$—$(CH_2CH_2O)_m$-G-$(CH_2CH_2O)_{m2}$—$(CR_xR_y)_{n4}$—

$R_x$ and $R_y$ at each occurrence is independently hydrogen or $C_1$-$C_4$ alkyl;

G is a bond or -$(G_1)_t$-, wherein $G_1$ at each occurrence is independently aryl, cycloakyl, heteroaryl, or heterocycle;

n1 and n2 are each independently 1-4;

m1, m2, n3, and n4 are each independently 0-10;

t is 1, 2, 3, or 4; and wherein $R_1$, $R_2$, $R_x$, $R_y$, and $G_1$ optionally are each independently substituted with one or more substituents selected from the group consisting of halogen, cyano, —OH, $C_1$-$C_6$ alkoxy, —COOH, $C_1$-$C_6$ alkoxycarbonyl, oxo, and amino.

In some embodiments, X is NH.

In some embodiments, X is NH, and $L_1$ and $L_2$ are —$CH_2$—. For example, the compound of formula (I) may have a structure of formula (I-a)

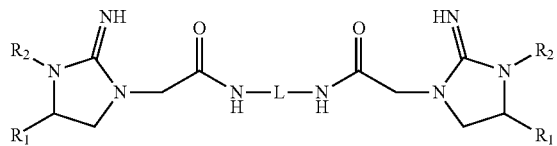

(I-a)

wherein $R_1$, $R_2$, and L are as defined above.

In some embodiments, the $R_1$ group of compounds of formula (I) or formula (I-a) is $C_1$-$C_{10}$ alkyl or aryl-$C_1$-$C_6$ alkyl. For example, $R_1$ may be a $C_2$-$C_{10}$ alkyl, a $C_4$-$C_8$ alkyl, or a phenyl-$C_1$-$C_6$ alkyl. In a particular embodiment, $R_1$ is a benzyl group.

In some embodiments, the $R_2$ group of compounds of formula (I) or formula (I-a) is $C_1$-$C_{10}$ alkyl, aryl-$C_1$-$C_6$ alkyl, or cycloalkyl-$C_1$-$C_6$ alkyl. For example, $R_2$ may be a $C_2$-$C_{10}$ alkyl, a $C_4$-$C_8$ alkyl, a phenyl-$C_1$-$C_6$ alkyl, a cyclohexyl-$C_1$-$C_6$ alkyl, or an adamantyl-$C_1$-$C_6$ alkyl. In some embodiments, $R_2$ is a $C_1$-$C_6$ alkyl group, such as $C_2$-$C_6$ or $C_4$-$C_6$ alkyl. In a particular embodiment, $R_2$ is a $C_6$ alkyl, such as —$(CH_2)_5CH_3$.

In some embodiments, m1, m2, and n4 are 0, G is a bond, and the L group of the compounds of formula (I) or formula (I-a) is —$(CR_xR_y)_{n3}$—. For example, the L group may be —$(CH_2)_{n3}$—. In some embodiments, the L group is —$(CH_2)_{n3}$— and n3 is 2, 3, 4, 5, 6, 7, or 8.

In some embodiments, m1, m2, n3, and n4 are 0, and the L group of the compounds of formula (I) or formula (I-a) is -$(G_1)_t$-. In some embodiments, L is -$(G_1)_t$-, in which $G_1$ is aryl and t is 1 or 2. For example, L may be

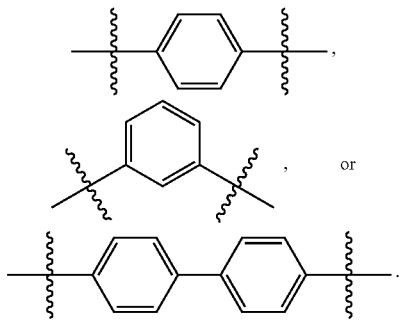

In a particular embodiment, L is

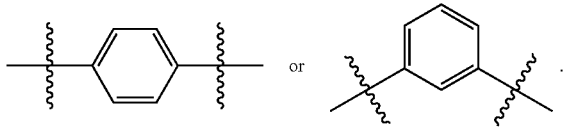 [SMILES: *c1ccc(*)cc1 ; *c1cccc(*)c1]

In some embodiments, m2 is 0, G is a bond, and the L group of the compounds of formula (I) or formula (I-a) is —$(CR_xR_y)_{n3}$—$(CH_2CH_2O)_{m1}$—$(CR_xR_y)_{n4}$—. In some embodiments, L is —$(CH_2)_{n3}$—$(CH_2CH_2O)_{m1}$—$(CH_2)_{n4}$—. In some embodiments, L is —$(CR_xR_y)_{n3}$—$(CH_2CH_2O)_{m1}$—$(CR_xR_y)_{n4}$—, in which m1, n3, and n4 are each independently 1, 2, 3, 4, 5, 6, 7, or 8. For example, L may be —$CH_2$—$(CH_2CH_2O)_3$—$CH_2CH_2CH_2$—.

In some embodiments, the bis-cyclic guanidine compounds may be synthesized by a representative process shown in Scheme 1.

Scheme 1

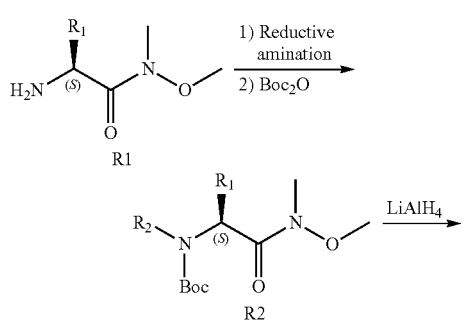

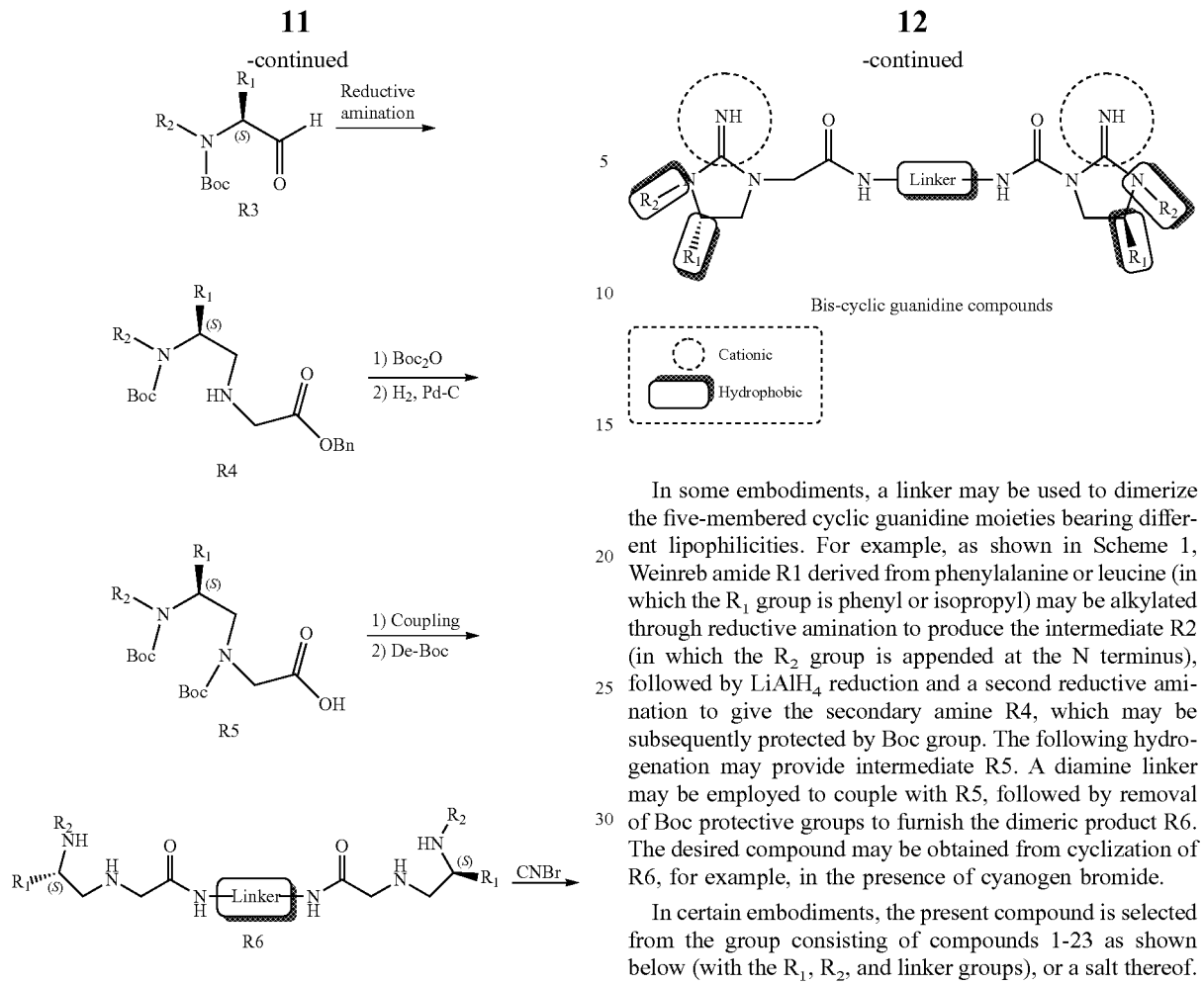

In some embodiments, a linker may be used to dimerize the five-membered cyclic guanidine moieties bearing different lipophilicities. For example, as shown in Scheme 1, Weinreb amide R1 derived from phenylalanine or leucine (in which the $R_1$ group is phenyl or isopropyl) may be alkylated through reductive amination to produce the intermediate R2 (in which the $R_2$ group is appended at the N terminus), followed by $LiAlH_4$ reduction and a second reductive amination to give the secondary amine R4, which may be subsequently protected by Boc group. The following hydrogenation may provide intermediate R5. A diamine linker may be employed to couple with R5, followed by removal of Boc protective groups to furnish the dimeric product R6. The desired compound may be obtained from cyclization of R6, for example, in the presence of cyanogen bromide.

In certain embodiments, the present compound is selected from the group consisting of compounds 1-23 as shown below (with the $R_1$, $R_2$, and linker groups), or a salt thereof.

-continued

| Compounds | R1 | R2 | Linker |
|---|---|---|---|
| 6 | benzyl | 3-phenylpropyl | 1,3-phenylene |
| 7 | benzyl | 3-phenylpropyl | 3-(cyanoamino)phenylene |
| 8 | benzyl | 3-phenylpropyl | 3-(ureido)phenylene |
| 9 | benzyl | 3-phenylpropyl | octamethylene |
| 10 | benzyl | 3-phenylpropyl | 4,4'-biphenylene |
| 11 | benzyl | n-hexyl | 4,4'-biphenylene |
| 12 | benzyl | n-hexyl | 1,3-phenylene |
| 13 | benzyl | n-hexyl | pentamethylene |
| 14 | benzyl | n-hexyl | heptamethylene |
| 15 | benzyl | n-hexyl | decamethylene |
| 16 | benzyl | n-hexyl | -(CH$_2$)$_3$-O-(CH$_2$CH$_2$O)$_2$-(CH$_2$)$_3$- |
| 17 | benzyl | n-octyl | 1,4-phenylene |

| Compounds | R1 | R2 | Linker |
|---|---|---|---|
| 18 | benzyl | n-octyl | meta-phenylene |
| 19 | benzyl | 2-cyclohexylethyl | para-phenylene |
| 20 | benzyl | 2-cyclohexylethyl | meta-phenylene |
| 21 | benzyl | adamantyl | para-phenylene |
| 22 | benzyl | adamantyl | meta-phenylene |
| 23 | isobutyl | n-hexyl | meta-phenylene |

3. Pharmaceutical Compositions

The bis-cyclic guanidine compounds disclosed herein may be incorporated into pharmaceutical compositions suitable for administration to a subject (such as a human or non-human subject).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of the present disclosure, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions typically are sterile and stable under the conditions of manufacture and storage.

The route by which a bis-cyclic guanidine compound disclosed herein is administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration may include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition may range from about 10 to about 90%, including from about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition may range from about 1% to about 20%, including from about 5% to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition may range from about 10% to about 90%, including from about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition may range from about 0.1% to about 10%.

Suitable colorants include a colorant such as an FD&C dye. When used, the amount of colorant in a systemic or topical composition may range from about 0.005% to about 0.1%.

Suitable flavors include menthol, peppermint, and fruit flavors. The amount of flavor(s), when used, in a systemic or topical composition may range from about 0.1% to about 1.0%.

Suitable sweeteners include aspartame and saccharin. The amount of sweetener(s) in a systemic or topical composition may range from about 0.001% to about 1%.

Suitable antioxidants include butylated hydroxyanisole ("BHA"), butylated hydroxytoluene ("BHT"), and vitamin E. The amount of antioxidant(s) in a systemic or topical composition may range from about 0.1% to about 5%.

Suitable preservatives include benzalkonium chloride, methyl paraben and sodium benzoate. The amount of preservative(s) in a systemic or topical composition may range from about 0.01% to about 5%.

Suitable glidants include silicon dioxide. The amount of glidant(s) in a systemic or topical composition range from about 1% to about 10%, including from about 1% to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition may range from 0% to about 100%.

Suitable suspending agents include AVICEL RC-591 (from FMC Corporation of Philadelphia, Pa.) and sodium alginate. The amount of suspending agent(s) in a systemic or topical composition may range from about 1% to about 10%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may range from about 0.1% to about 10%, including from about 0.1% to about 5%.

Although the amounts of components in the systemic compositions may vary depending on the type of systemic composition prepared, in general, systemic compositions include 0.01% to 50% of active compound and 50% to 99.99% of one or more carriers. Compositions for parenteral administration may include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount of a bis-cyclic guanidine compound disclosed herein, usually at least about 0.1% by weight, including, for example, from about 1% to about 99%, from about 5% to about 95%, and from about 25% to about 75%. The oral dosage compositions may include from about 0.1% to about 99.9% by weight of carriers, including, for example, from about 1% to about 99%, from about 5% to about 95%, from about 10% to about 90%, from about 25% to about 75%, and from about 50% to about 75%.

Tablets can be compressed, tablet triturates, enteric-coated, sugar-coated, film-coated, or multiple-compressed. Tablets may include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) may include an active compound, and a carrier including one or more diluents disclosed above in a capsule comprising gelatin. Granules may comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings may include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions may include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions may include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions may include an active compound (such as a bis-cyclic guanidine compound disclosed herein) and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may range from about 5% to about 95%.

Suitable propellants include propane, butane, isobutane, dimethyl ether, carbon dioxide, nitrous oxide, and combinations thereof. The amount of propellant(s) in a topical composition may range from 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition may range from 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition may range from 0% to about 95%.

The amount of thickener(s) in a topical composition may range from 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may range from 0% to about 95%.

The amount of fragrance in a topical composition may range from 0% to about 0.5%, including, for example, from about 0.001% to about 0.1%.

Suitable pH adjusting additives include HCl or NaOH in amounts sufficient to adjust the pH of a topical pharmaceutical composition.

4. Methods of Treatment

The bis-cyclic guanidine compounds disclosed herein may be used in methods for treatment of bacterial infections. Without being limited by any theory, it is hypothesized that the bis-cyclic guanidine compounds disclosed herein are endowed with the ability of bacterial membrane action by incorporating hydrophobic residues, and their overall structures are amphipathic with positive charges, and therefore they may interact with bacterial membrane effectively. Since the guanidine groups may be cationic charged, it is further hypothesized that a number of hydrophobic groups both on side chain and linker may be used to adjust the overall amphiphilicity of the compounds.

The disclosed compounds may contain antimicrobial activities against a panel of medicinally relevant Gram-positive and three Gram-negative bacteria, including multi-drug resistant strains. The disclosed compounds may exhibit exceptional potency and broad-spectrum activity. In some embodiments, the disclosed compounds may contain substantial in vivo efficacy. For example, the disclosed compounds may show in vivo efficacy in an animal model, such as a thigh-infection mouse model. In some embodiments, the compounds disclosed herein may inhibit infection caused by drug-resistant bacteria, and may be used to combat prevalence of bacterial resistance.

In some embodiments, the present compounds may be used to treat infections caused by clinically relevant bacteria, including but not limited to multidrug resistant Gram-positive and Gram-negative bacterial pathogens. Without being limited by any theory, it is hypothesized that the hydrophobic groups on the cyclic guanidine compounds may affect the hydrophobic interaction of these compounds with bacteria membranes. As a non-limiting illustration, compounds without hydrophobic groups on the cyclic guanidine ring may not lead to strong hydrophobic interaction with bacteria membranes, even although they may reach on the surface of negatively charged bacteria through electrostatic interactions. Further, appending hydrophobic groups onto the cyclic guanidine ring may enhance the interaction of these compounds to associate with bacterial membranes.

The methods of treatment may comprise administering to a subject in need of such treatment a composition comprising a therapeutically effective amount of a bis-cyclic guanidine compound disclosed herein. These methods of treatment disclosed herein may treat the bacterial infection by inducing bacterial cytotoxicity. The methods of treatment disclosed herein may treat the bacterial infection by preventing the formation of bacterial biofilms.

In some embodiments, the disclosed compound may be used to treat infections caused by *K. pneumoniae, P. aeruginosa, E. coli*, vancomycin-resistant *Enterococcus faecalis*, Methicillin-resistant *S. aureus* (MRSA), or Methicillin-resistant *S. epidermidis* (MRSE). In some embodiments, substituents on the cyclic guanidine ring may improve the antibacterial activity, such as activity against Gram-negative bacteria *E. coli*.

In some embodiments, the disclosed compounds may have antibacterial activity toward MRSA, and may be used to treat infection caused by MRSA. In some embodiments, the disclosed compounds may be used to treat bacterial infections caused by bacteria that form a bacterial biofilm. For example, the bacterial biofilm formed by MRSA or *E. coli* bacteria.

In some embodiments, the disclosed compounds may be used to treat a bacterial infection that is resistant to treatment with one or more antibiotics.

The compositions disclosed herein may be useful for treating bacterial infections in humans and animals. Treatment of such infections may be effected by killing bacteria and/or preventing, slowing, or stopping the formation of bacterial biofilms, by administering a compound of composition of this disclosure, either alone or in combination with another active agent as part of a therapeutic regimen to a subject in need thereof.

Thus, administering a therapeutically effective amount of the bis-cyclic guanidine compounds and compositions disclosed herein may serve to eliminate bacterial infection in subjects. Specifically, the bis-cyclic guanidine compounds and compositions disclosed herein may be useful for treating MRSA infections and drug-resistant bacterial infections.

a. Bacterial Infections

Although bacteria may not be harmful, and in some cases may be beneficial, bacteria may also lead to infection. Bacterial infections can affect multiple organs and body systems including, but not limited to, skin, mucous membranes, blood, lungs, kidneys, urinary tract, eyes, heart, intestines, meninges, respiratory tract, genitals, stomach, bone, connective tissue, and tissue surrounding organs. Bacterial infections may affect more than one organ or body system. Bacterial infections may be systemic. Bacterial infections may be asymptomatic. Bacterial infections may cause a variety of symptoms including, but not limited to, fever, inflammation, wounds that do not heal, weeping wounds, skin rash, red bumps on the skin, abscesses, swollen lymph nodes, nausea, diarrhea, headaches, earaches, sore throat, fatigue, low blood pressure, hyperventilation, weak and rapid pulse, local or systemic pain, and muscle aches. Bacterial infections may cause death. Subjects with co-morbidities or a compromised immune system may be more susceptible to bacterial infections.

The diagnosis of a bacterial infection may include, but are not limited to, symptomatic diagnostics, microbial culture, microscopy, biochemical tests, PCR based diagnostics, and metagenomics sequencing. A microbial examination may include sample collection, microbial cultivation, identification, and test of antibiotic susceptibility. The diagnosis may include gram staining of the bacterial culture. The diagnosis may include a coagulase test of the bacterial culture. The diagnosis may include a catalase test of the bacterial culture. The diagnosis may include blood tests. The blood tests may include, but are not limited to, a full blood count, measurement of C-reactive protein, measurement of procalcitonin, and measurement of rapid plasma reagin. The diagnosis may include ELISA. The diagnosis may include PCR. A rapid latex agglutination test that detects the PBP2a protein may be conducted to identify MRSA. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The determination of bacteria growing on an agar plate or in a nutrient broth may determine the bacteria responsible for the subject's infection. Discs containing antibiotic compounds may be placed on the agar plates. The antibiotic compounds may kill the bacteria growing on the plate. The greater the zone of dead bacteria around the disc (zone of inhibition) may indicate a more effective antibiotic.

Samples for diagnosing a bacterial infection may be obtained from the subject in need of treatment. The sample for testing may be from the site of the infection. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

Bacterial infections may be treated with the bis-cyclic guanidine compounds and compositions disclosed herein. Bacterial infections that may be treated by the bis-cyclic guanidine compounds and compositions disclosed herein include, but are not limited to, *Staphylococcus aureus*, methicillin-resistant *Staphylococcus aureus* (MRSA), Methicillin-resistant *S. epidermidis* (MRSE), *Enterococcus faecalis, Enterococcus faecium, Escherichia coli, Salmonella, Neisseria, Bacillus, Brucella, Nocardia, Listeria monocytogenes, Lactobacillus plantarum, Lactococcus lactis, Francisella, Legionella,* and *Yersinia pestis, K. pneumoniae, Pseudomonas aeruginosa, Burkholderia cenocepacia,* and *Mycobacterium avium*. The bacterial infection to be treated may be resistant to one or many antibiotics. The bacterial infection to be treated may be caused by bacteria that form bacterial biofilms.

i) MRSA Infections

MRSA is any strain of *Staphylococcus aureus* that has developed multi-resistance to beta-lactam antibiotics, which include the penicillins (methicillin, dicloxacillin, nafcillin, oxacillin, etc.) and the cephalosporins. MRSA evolved from horizontal gene transfer of the mecA gene to at least five distinct *S. aureus* lineages. MRSA infections can quickly cause serious and life threatening internal infections including, but not limited to, sepsis, endocarditis, MRSA pneumonia bone infections, and infections of implants. MRSA may cause infections of the skin. The MRSA skin infections may lead to boils or abscesses. MRSA may cause systemic or internal infections. Some MRSA infections are untreatable with currently available antibiotics, usually resulting in severe, debilitating infection, or death. The MRSA infection may occur in subjects who have been hospitalized, which is known as health care-associated MRSA (HA-MRSA). The MRSA infection may be spread by skin-to-skin contact, which is known as community-associated MRSA (CA-MRSA). Cases of MRSA have increased in livestock animals. CC398, a variant of MRSA, has emerged in animals and is found in intensively reared production animals (e.g., pigs, cattle, and poultry), where it can be transmitted to humans as LA-MRSA (livestock-associated MRSA).

The strains of MRSA to be treated by the bis-cyclic guanidine compounds and compositions disclosed herein may include, but are not limited to, CBD-635, ST250 MRSA-1, ST2470-MRSA-I, ST239-MRSA-III, ST5-MRSA-II, ST5-MRSA-IV, ST239-MRSA-III, EMRSA15, EMRSA16, MRSA252, ST5:USA100, EMRSA 1, ST8: USA300, ST1:USA400, ST8:USA500, ST59:USA1000, USA1100, USA600, USA800, USA300, ST30, ST93, ST80, ST59, CC22, CC8, CC425, and CC398.

ii) Bacterial Biofilms

A biofilm is known as a structured consortium attached on a living or inert surface formed by microbial cells sticking to each other and surrounded by an extracellular polymeric matrix that is produced by the microbes. The development of a biofilm may include several stages. The stages may include attachment to a surface, formation of microcolonies, development of young biofilm, differentiation of structured mature biofilm, and dispersal of mature biofilm. Biofilm bacterial cells may be significantly more resistant to antibiotics and host immune defense than bacteria of the same species growing outside of a biofilm.

Bacterial biofilm formation is widely found in natural environments with water, and also in human diseases, especially in the subjects with indwelling devices for the purpose of medical treatments. It has been reported that the vast majority, if not all, of the medical devices or prostheses may result in biofilm infections. The medical devices or prostheses which may form biofilms include, but are not limited to, intravenous catheters, vascular prosthesis, cerebrospinal fluid shunts, prosthetic heart valves, urinary catheters, joint prostheses and orthopedic fixation devices, cardiac pacemakers, peritoneal dialysis catheters, intrauterine devices, biliary tract stents, dentures, breast implants, contact lenses, and in the dental area caries and periodontitis. Bacterial biofilm infections that are not associated with foreign bodies may also occur. Bacterial biofilm infections may include but are not limited to, chronic airway infections in subjects with cystic fibrosis (CF) or chronic obstructive pulmonary diseases, native valve endocarditis, chronic otitis media, chronic sinusitis, chronic wound infections, and diabetic wound infections. It has been estimated that most bacterial infections in human are correlated with biofilm and about 50% of the nosocomial infections are indwelling devices-associated.

Bacteria that may form biofilms include, but are not limited to, methicillin-resistant *Staphylococcus aureus, Staphylococcus aureus, Bacillus* spp, *Listeria monocytogenes, Lactobacillus plantarum, Lactococcus lactis, Escherichia coli,* and *Pseudomonas aeruginosa*.

The bis-cyclic guanidine compounds and compositions described herein may demonstrate modes of action toward eliminating bacterial infection, including preventing biofilm formation. The present compounds or compositions thereof may be administered to a subject in need thereof to reduce, render bacteriostatic, eliminate, or otherwise inhibit infection, such as a MRSA biofilm infection. For example, the composition may reduce the area of infection, improve recovery from infection, prevent worsening of infection, or even prevent occurrence of infection in the subject in need thereof after administration of the composition.

b. Modes of Administration

Methods of treatment may include any number of modes of administering a disclosed composition. Modes of administration may include tablets, pills, dragees, hard and soft gel capsules, granules, pellets, skin patches, skin creams, skin gels, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the compounds or compositions disclosed herein may be admixed with adjuvants and excipients, such as gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the compounds or compositions disclosed herein may also be dispersed in a microparticle, e.g. a nanoparticulate composition.

For parenteral administration, the compounds or compositions disclosed herein may be dissolved or suspended in a physiologically acceptable diluent, such as water, buffer, oils with or without solubilizers, surface-active agents, dispersants or emulsifiers. Suitable oils may include, for example, olive oil, peanut oil, cottonseed oil, soybean oil, castor oil and sesame oil. For parenteral administration, the compounds or compositions disclosed herein may be administered in the form of an aqueous, lipid, oily or other kind of solution or suspension, or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

The bis-cyclic guanidine compounds and compositions disclosed herein may be administered topically. A topical composition disclosed herein may be applied to the skin of a subject in need thereof. The area of skin selected for treatment may be the site of a bacterial infection. The area of skin selected for treatment may be skin surrounding the infection site. The area of skin selected for treatment may be the site of a bacterial infection and the skin surrounding the infection site. The infection of the skin may be caused by MRSA. A topical composition disclosed herein may be applied to a mucous membrane of a subject in need thereof. The mucous membrane selected for treatment may be the site of a bacterial infection. The area of the mucous membrane selected for treatment may be the mucous membrane surrounding the bacterial infection. The mucous membrane selected for treatment may be the site of a bacterial infection and the mucous membrane surrounding the site of the infection. The infection of the mucous membrane may be caused by MRSA.

The topical administration may be with a patch containing the compounds and compositions disclosed herein. The topical administration may be with a dissolvable patch containing the compounds and compositions disclosed herein. The topical administration may be with a cream containing the compounds and compositions disclosed herein. The topical administration may be with foam containing the compounds and compositions disclosed herein. The topical administration may be with lotion containing the compounds and compositions disclosed herein. The topical administration may be with an ointment containing the compounds and compositions disclosed herein. The topical administration may be with gel containing the compounds and compositions disclosed herein. The topical administration may have fewer side effects than systemic administration of antibiotics.

In some embodiments, a topical composition comprising a therapeutically effective amount of the bis-cyclic guanidine compounds and compositions disclosed herein may be applied to the infected skin and/or mucous membrane of a subject to reduce or eliminate the infection, and/or improve healing of the wounded skin and/or mucous membrane. In particular embodiments, a topical composition comprising a therapeutically effective amount of the bis-cyclic guanidine compounds and compositions disclosed herein may be applied to an area of the skin and/or mucous membrane infected by MRSA, including infections caused by MRSA biofilm. In these embodiments, the bis-cyclic guanidine compounds and compositions disclosed herein may be administered alone or in combination of one or more other active agents to reduce infection and/or promote skin and/or mucous membrane healing.

The bis-cyclic guanidine compounds and compositions disclosed herein may be administered transdermally using known methods. For example, the disclosed compounds may be administered by a transdermal patch applied to the skin of a subject.

c. Combination Therapies

Additional therapeutic agent(s) may be administered simultaneously or sequentially with the present compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present disclosure.

For the treatment of bacterial infection, the present compounds and compositions may be combined with a variety of antibiotics. The antibiotics include, but are not limited to, vancomycin, linezolid, teicoplanin, clindamycin, mupirocin, trimethoprim-sulfamethoxazole, tetracyclines, daptomycin, sulfa drugs, ceftobiprole, ceftaroline, dalbavancin, telavancin, torezolid, iclaprim, nemonoxacin, platensimycin, and oxadiazoles.

The present compounds and compositions may be combined with agents that inhibit bacterial biofilm formation. The agents that inhibit bacterial biofilm formation include, but are not limited to, imidazole derivatives, indole derivatives, emodin, flavonoids, ginger extracts, *Hypericum perforatum,* 7-epiclusianone, isolimonic acid, tannic acid, chelerythrine, carvacrol, bgugaine, resveratrol, garlic extracts, natural halogenated furanones, brominated alkylidene lactams, and AHLs-based inhibitors.

The present compounds and compositions may be combined with lysine-conjugated aliphatic norspermidine analogues. The present compounds and compositions may be combined with phage therapy. In the case of infection involving a medical device or prosthesis, the present compounds and compositions may be administered in combination with the removal of the medical device or prosthesis. A new, sterile medical device or prosthesis may be implanted in the subject.

The present compounds and compositions may be combined with agents to modify potential side effects from antibacterial agents. Agents that may mediate or treat side effects include, but are not limited to, probiotics, anti-diarrheal agents, anti-emetic agents, and analgesics.

The subject may also be undergoing a variety of treatments for co-morbidities.

d. Evaluation of Treatment

The efficacy of the methods of treatment with the bis-cyclic guanidine compounds and compositions disclosed herein may be measured. The status of the bacterial infection may be monitored. The efficacy of the methods of treatment disclosed herein may be evaluated by the same or similar methods as used for diagnosis of the bacterial infection.

Evaluating the efficacy of the methods of treatment with the bis-cyclic guanidine compounds and compositions disclosed herein or monitoring the bacterial infection may include, but are not limited to, symptomatic diagnostics, microbial culture, microscopy, biochemical tests, PCR based tests, and metagenomics sequencing. A microbial examination may include sample collection, microbial cultivation, identification, and test of antibiotic susceptibility. The evaluation or monitoring may include gram staining of the bacterial culture. The evaluation or monitoring may include a coagulase test of the bacterial culture. The evaluation or monitoring may include a catalase test of the bacterial culture. The evaluation or monitoring may include blood tests. The blood tests may include, but are not limited to, a full blood count, measurement of C-reactive protein, measurement of procalcitonin, and measurement of rapid plasma reagin. The evaluation or monitoring may include ELISA. The evaluation or monitoring may include PCR. A rapid latex agglutination test that detects the PBP2a protein may be conducted to identify MRSA. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The presence, decreased presence, or lack of bacteria growing on an agar plate or in a nutrient broth may determine that the bacterial infection is improving or has been eradicated.

Samples for determining the efficacy of the methods of treatment with the bis-cyclic guanidine compounds and compositions disclosed herein or monitoring the bacterial infection, may be obtained from the subject. The sample for testing may be from the site of the infection, or the site where the infection was previously present. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

The evaluation of the efficacy of methods of treatment with the bis-cyclic guanidine compounds and compositions disclosed herein or monitoring of the bacterial infection may indicate that the subject requires continued treatment with the bis-cyclic guanidine compounds and compositions disclosed herein. The evaluation of the efficacy of methods of treatment with bis-cyclic guanidine compounds and compositions disclosed herein or monitoring of the bacterial infection may indicate the eradication of the bacterial infection in the subject. The eradication of the bacterial infection may indicate that the subject no longer requires treatment with the bis-cyclic guanidine compounds and compositions disclosed herein.

5. Kits

The bis-cyclic guanidine compounds disclosed herein may be included in kits comprising the compound, a systemic or topical composition, or both; and information, instructions, or both that use of the kit will provide treatment for medical conditions in mammals (particularly humans). The kit may include an additional pharmaceutical composition for use in combination therapy. The kit may include buffers, reagents, or other components to facilitate the mode of administration. The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

6. Examples

General Information. α-Phenylalanine and α-Leucine were purchased from Chem-Impex International, Inc. Solvents and other reagents were purchased from either Sigma-Aldrich or Fisher Scientific and were used without further purification. The final products were purified on a Waters Breeze 2 HPLC system, and lyophilized on a Labconco lyophilizer. The purity of the compounds was determined to be >95% by analytical HPLC (1 mL/min flow, a 5% to 100% linear gradient of solvent B (0.1% TFA in acetonitrile) in A (0.1% TFA in water) over 50 min was used). The NMR spectra were obtained on Varian Inova 500 and 600 instruments.

Example 1. Synthesis of Bis-Cyclic Guanidine Compounds

A synthesis route for compound 21, representative of the compounds disclosed herein, is shown in Scheme 2. Crude compounds were analyzed and prepared on Waters HPLC system, followed by lyophilization to give the pure products.

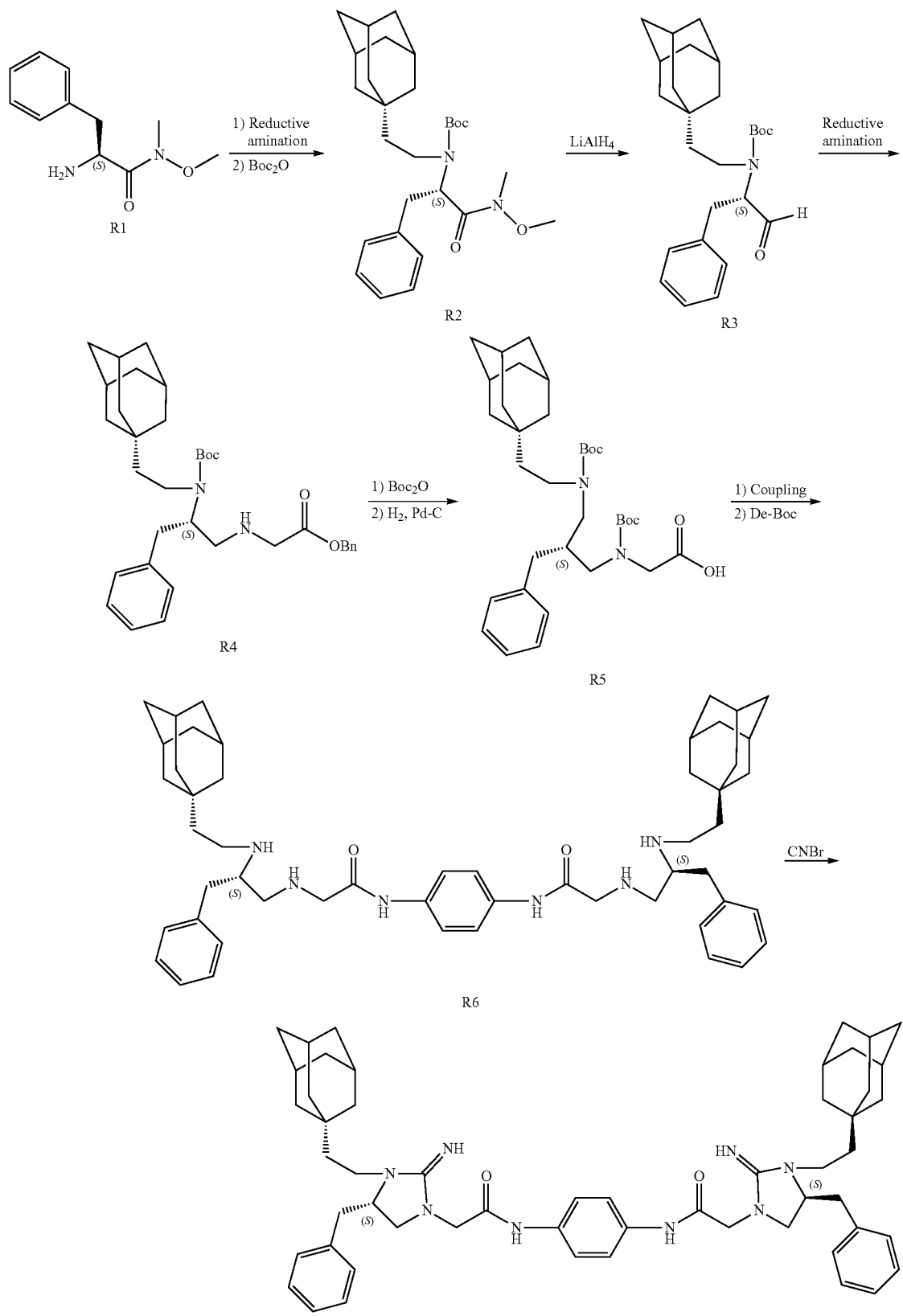
Scheme 2
Cyclic Guanidine Dimer 21

Compound R1 (TFA salt, 10.8 g, 33.6 mmol) was dissolved in MeOH and treated with TFA (5.1 mL, 33.6 mmol) before adding to a solution of 2-((3R,5R,7R)-adamantan-1-yl) acetaldehyde (6 g, 33.6 mmol) in MeOH and acetic acid (2 mL, 67.2 mmol). After stirring 10 min under ice/$H_2O$ bath, $NaBH_3CN$ (3.2 g, 50.4 mmol) was added portion wise. The reaction was stirred for 3 h at room temperature before solvent was removed. The crude mixture was treated with $NaHCO_3$ (aq.) and extracted with EtOAc, and the organic layer was separated and evaporated to give oil crude, which was purified by silica gel column chromatography to give 8.2 g of the $2^{nd}$ amine. $Boc_2O$ (7 g, 32.4 mmol) was added in the $THF/H_2O$ (1:1, v/v) solution of this intermediate containing $NaHCO_3$ (3.6 g, 43.2 mmol) and allowed to react for 5 h, after which EtOAc was added and organic layer was collected and removed in reduced vacuum to give colorless crude, which was purified by flash column chromatography to give 8.5 g of compound R2. Compounds R2 was taken in THF and reduced by $LiAlH_4$ (687 mg, 18 mol) for 30 min at −20 OC, water was then added. The mixture was extracted with EtOAc, and the organic layer was separated and the solvent was removed under reduced vacuum to give crude R3, which was used in the next reaction without any further purification. Compound R3 was converted into compound R4 with same procedure as in making compound R2. BOC protecting group was attached as the same procedure for attaching BOC on compound R2, followed by hydrogenation to remove benzyl protecting group in MeOH to give building block R5 as white solid after filtration and concentration.

Building block R5 (300 mg, 0.52 mmol), HOBt (159 mg, 1.04 mmol), DIPEA (129 L, 1.04 mmol), and m-Phenylenediamine (34 mg, 0.32 mmol) was dissolved in DMF (2 mL) and then DCC (214 mg, 1.04 mmol) was added. The reaction mixture was stirred at room temperature for 24 h. The afforded byproduct DCU was filtered and the filtration was added into water and extracted with EtOAc (×3). The organic phase was combined and washed with 1M HCl (×2), dried over anhydrous $Na_2SO_4$, filtrated, and concentrated under reduced vacuum. The crude oil compound was treated with TFA in DCM (1:1, v/v) for 2 h to completely remove BOC protecting groups to yield crude compound R6, which was dissolved in acetonitrile (3 mL) without purification, to which CNBr (4 eq.) was added carefully. The reaction was stirred for 12 h at room temperature. 1M NaOH solution was added carefully, followed by proper amount of bleach to deactivate excessive CNBr. The mixture was filtered through Millipore filter and purified by HPLC purification on Waters HPLC system, and the desired fraction was lyophilized to give the pure product 21.

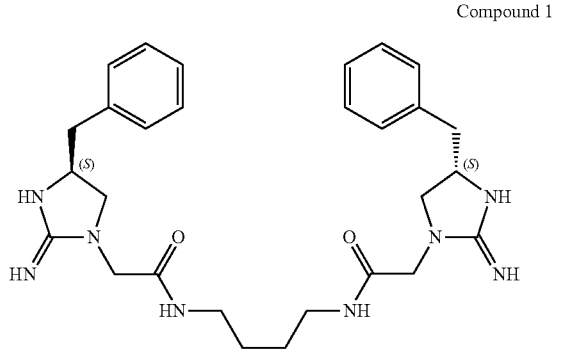

Compound 1

Compound 1. $^1$H NMR (500 MHz, $CD_3OD$) δ 7.31-7.34 (m, 4H), 7.22-7.26 (m, 6H), 4.22-4.28 (m, 2H), 3.94, 3.98 (ABq, $J_{AB}$=12.0 Hz, 4H), 3.72 (t, J=9.5 Hz, 2H), 3.42 (dd, J=9.0, 6.0 Hz, 2H), 3.22 (t, J=5.5 Hz, 4H), 2.93 (ddd, J=15.0, 14.0, 7.0 Hz, 4H), 1.54 (dtt, J=9.0, 6.0, 3.5 Hz, 4H). $^{13}$C NMR (125 MHz, $CD_3OD$) δ 167.0, 159.2, 136.1, 128.9 (2C), 128.4 (2C), 126.7, 54.5, 53.2, 46.2, 40.2, 38.7, 26.2. HRMS (ESI) $C_{28}H_{39}N_8O_2$ $[M+H]^+$ calcd=519.3190; found=519.3193.

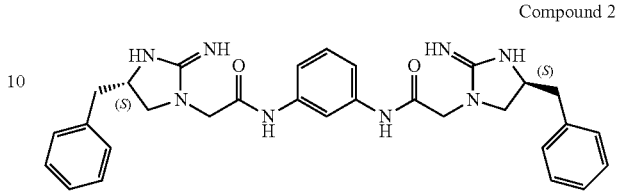

Compound 2

Compound 2. $^1$H NMR (500 MHz, $CD_3OD$) δ 8.05 (s, 1H), 7.31-7.34 (m, 4H), 7.22-7.27 (m, 9H), 4.25-4.30 (m, 2H), 4.14, 4.19 (ABq, $J_{AB}$=18.0 Hz, 4H), 3.79 (t, J=9.0 Hz, 2H), 3.50 (dd, J=9.5, 5.5 Hz, 2H), 2.93 (ddd, J=15.0, 13.5, 6.5 Hz, 4H), 1.54 (dtt, J=9.0, 6.0, 3.5 Hz, 4H). $^{13}$C NMR (125 MHz, $CD_3OD$) δ 165.2, 159.3, 138.5, 136.1, 128.9 (2C), 128.4 (2C), 126.7, 115.4, 111.2, 54.6, 53.3, 46.5, 40.3. HRMS (ESI) $C_{30}H_{35}N_8O_2$ $[M+H]^+$ calcd=539.2877; found=539.2877.

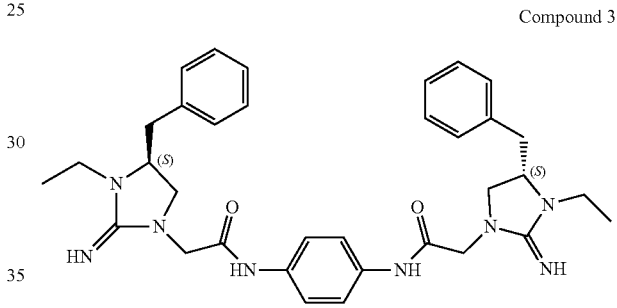

Compound 3

Compound 3. $^1$H NMR (500 MHz, $CD_3OD$) δ 7.52 (brs, 4H), 7.31-7.33 (m, 4H), 7.22-7.28 (m, 6H), 4.29-4.34 (m, 2H), 4.14, 4.10 (ABq, J=18.0 Hz, 4H), 3.65 (t, J=11.5 Hz, 2H), 3.53-3.61 (m, 2H), 3.38-3.45 (m, 4H), 3.21 (dd, J=13.5, 4.5 Hz, 2H), 2.86 (dd, J=13.5, 8.5 Hz, 2H), 1.26 (t, J=7.5 Hz, 6H). $^{13}$C NMR (125 MHz, $CD_3OD$) δ 165.1, 157.9, 135.7, 134.3, 128.9 (2C), 128.5 (2C), 126.8, 120.1 (2C), 57.8, 51.8, 37.8, 37.5, 11.2. HRMS (ESI) $C_{34}H_{43}N_8O_2$ $[M+H]^+$ calcd=595.3503; found=595.3488.

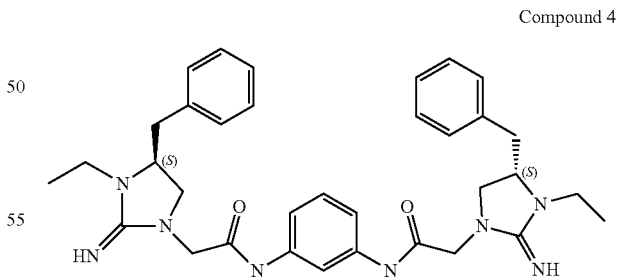

Compound 4

Compound 4. $^1$H NMR (500 MHz, $CD_3OD$) δ 8.05 (d, J=1.5 Hz, 1H), 7.31-7.34 (m, 4H), 7.23-7.28 (m, 9H), 4.28-4.34 (m, 2H), 4.15, 4.11 (ABq, J=17.5 Hz, 4H), 3.63 (t, J=9.5 Hz, 2H), 3.56 (quintet, J=6.5 Hz, 2H), 3.36-3.44 (m, 4H), 3.21 (dd, J=13.5, 4.5 Hz, 2H), 2.85 (dd, J=13.5, 9.0 Hz, 2H), 1.26 (t, J=7.0 Hz, 6H). $^{13}$C NMR (125 MHz, $CD_3OD$) δ 165.2, 157.9, 138.5, 135.7, 129.0 (2C), 128.4 (2C), 126.8, 115.4, 111.2, 57.8, 51.7, 37.8, 37.6, 11.2. HRMS (ESI) $C_{34}H_{43}N_8O_2$ $[M+H]^+$ calcd=595.3503; found=595.3490.

Compound 5

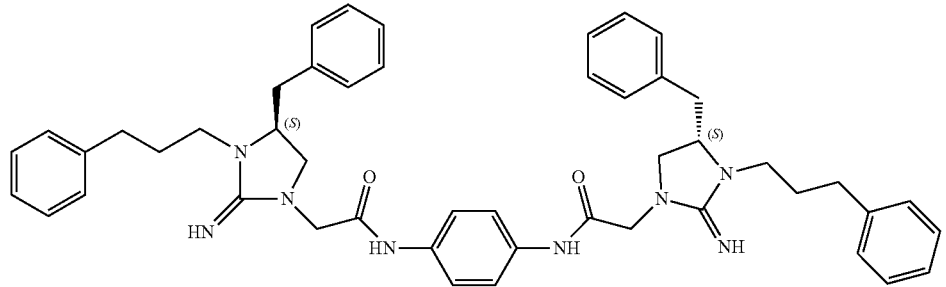

Compound 5. ¹H NMR (500 MHz, CD₃OD) δ 7.53 (s, 4H), 7.17-7.32 (m, 20H), 4.22-4.27 (m, 2H), 4.0 (s, 4H), 3.60 (t, J=9.5 Hz, 2H), 3.50-3.57 (m, 2H), 3.40 (dd, J=9.5, 5.0 Hz, 2H), 3.33 (dd, J=8.5, 5.5 Hz, 2H), 3.08 (dd, J=13.5, 5.0 Hz, 2H), 2.83 (dd, J=13.5, 8.0 Hz, 2H), 2.61-2.73 (m, 4H), 1.91-2.05 (m, 4H). ¹³C NMR (125 MHz, CD₃OD) δ 165.0, 158.0, 140.9, 135.7, 134.3, 128.9 (2C), 128.4 (2C), 128.2 (2C), 128.0 (2C), 126.8, 125.8, 120.0, 58.0, 51.6, 42.4, 37.4, 32.1 (2C), 28.3. HRMS (ESI) $C_{48}H_{55}N_8O_2$ [M+H]⁺ calcd=775.4442; found=775.4443.

Compound 7. ¹H NMR (600 MHz, CD₃OD) δ 7.71 (t, J=1.8 Hz, 1H), 7.16-7.30 (m, 13H), 7.01 (dq, J=8.4, 1.0 Hz, 1H), 4.20-4.24 (m, 1H), 4.07 (d, J=6.6 Hz, 2H), 3.59 (td, J=10.8, 3.0 Hz, 1H), 3.50 (quintet, J=7.2 Hz, 1H), 3.38 (dd, J=10.8, 5.4 Hz, 1H), 3.30-3.32 (m, 1H), 3.06 (dd, J=13.8 Hz, 5.4 Hz, 1H), 2.80-2.84 (m, 1H), 2.60-2.69 (m, 2H), 1.92-1.99 (m, 2H). ¹³C NMR (150 MHz, CD₃OD) δ 165.0, 158.0, 140.8, 140.0, 138.3, 135.7, 128.9 (2C), 128.4 (2C), 128.2 (2C), 128.0 (2C), 126.8, 125.8, 114.8, 113.7, 110.5, 58.0, Compound 6

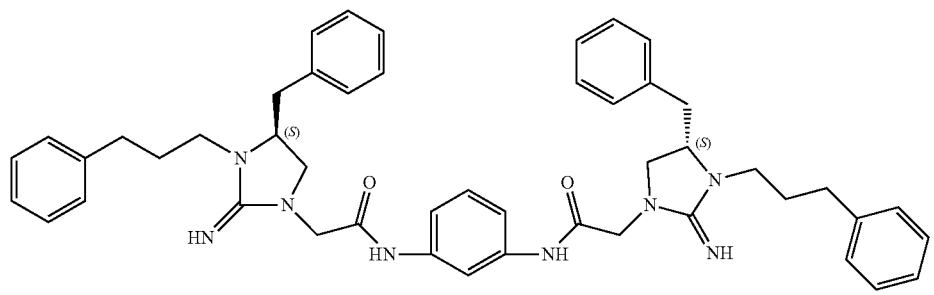

Compound 6. ¹H NMR (500 MHz, CD₃OD) δ 8.05-8.12 (m, 1H), 7.17-7.32 (m, 23H), 4.19-4.25 (m, 2H), 4.12, 4.09 ((ABq, $J_{AB}$=18.0 Hz, 4H), 3.60 (t, J=8.5 Hz, 2H), 3.52 (quintet, J=7.5 Hz, 2H), 3.39 (dd, J=9.5, 5.0 Hz, 2H), 3.27-3.33 (m, overlapped with CD₃OD, 2H), 3.07 (dt, J=13.5 Hz, 5.4 Hz, 2H), 2.82 (ddd, J=13.0, 9.0, 3.0 Hz, 2H), 2.60-2.72 (m, 4H), 1.92-2.02 (m, 4H). ¹³C NMR (125 MHz, CD₃OD) δ 165.2, 158.0, 140.8, 138.5, 135.6, 129.0 (2C), 128.4 (2C), 128.2 (2C), 128.0 (2C), 126.8, 125.8, 115.3, 58.0, 51.6, 42.3, 37.4, 32.1 (2C), 28.3. HRMS (ESI) $C_{48}H_{55}N_8O_2$ [M+H]⁺ calcd=775.4442; found=775.4438.

Compound 7

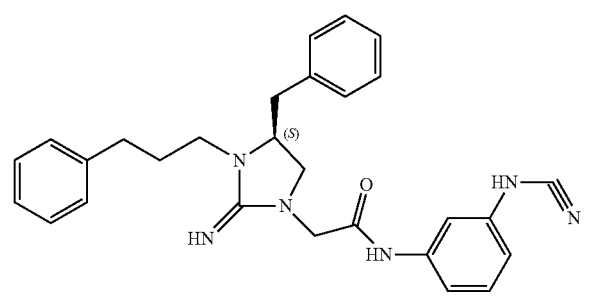

51.6, 42.4, 37.4, 32.1 (2C), 28.2. HRMS (ESI) $C_{28}H_{31}N_6O$ [M+H]⁺ calcd=467.2554; found=467.2550.

Compound 8

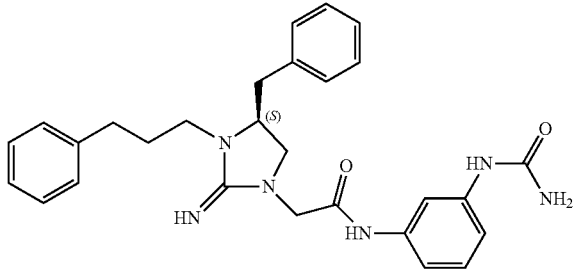

Compound 8. ¹H NMR (500 MHz, CD₃OD) δ 8.05-8.12 (m, 1H), 7.17-7.32 (m, 13H), 7.01 (dq, J=7.0, 1.0 Hz, 1H), 4.19-4.25 (m, 1H), 4.12, 4.09 (ABq, J=19.5 Hz, 2H), 3.59 (td, J=9.5, 1.0 Hz, 1H), 3.51 (quintet, J=7.5 Hz, 1H), 3.39 (dd, J=9.5, 5.0 Hz, 1H), 3.27-3.33 (m, overlapped with CD₃OD, 1H), 3.06 (dt, J=13.5 Hz, 4.5 Hz, 1H), 2.80-2.85 (m, 1H), 2.60-2.71 (m, 2H), 1.92-2.02 (m, 2H). ¹³C NMR (125 MHz, CD₃OD) δ 170.3, 165.0, 158.0, 140.8, 139.0, 138.3, 135.7, 129.0 (2C), 128.7, 128.4 (2C), 128.2 (2C), 128.0 (2C), 126.8, 125.8, 115.6, 115.1, 111.4, 58.0, 51.6, 42.4, 37.4, 32.1, 28.3, 22.4. HRMS (ESI) $C_{28}H_{32}N_6O_2$ [M]⁺ calcd=484.2587; found=484.2717.

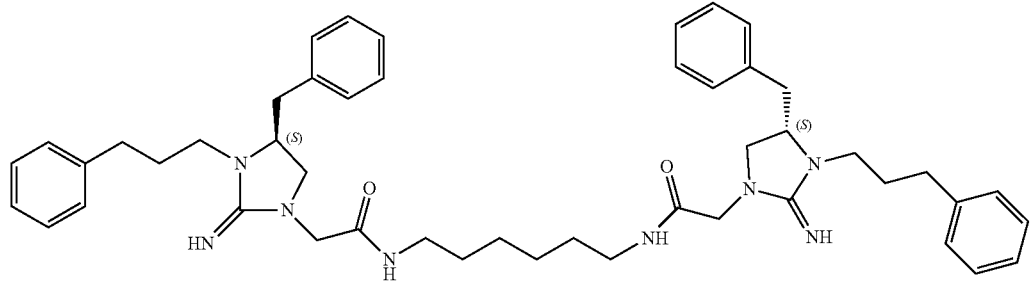

Compound 9

Compound 9. $^1$H NMR (500 MHz, CD$_3$OD) δ 7.17-7.32 (m, 20H), 4.18-4.23 (m, 2H), 3.90 (s, 4H), 3.60 (t, J=8.5 Hz, 2H), 3.47-3.52 (m, 4H), 3.27-3.33 (m, overlapped with CD$_3$OD, 2H), 3.18 (t, J=7.5 Hz, 4H), 3.06 (dd, J=13.5, 9.5 Hz, 2H), 2.80 (dd, J=13.5, 8.0, 3.0 Hz, 2H), 2.60-2.70 (m, 4H), 1.88-2.02 (m, 4H), 1.50 (quintet, J=7.5 Hz, 4H), 1.34 (quintet, J=7.5 Hz, 4H). $^{13}$C NMR (125 MHz, CD$_3$OD) δ 165.2, 158.0, 140.8, 138.5, 135.6, 129.0 (2C), 128.4 (2C), 128.2 (2C), 128.0 (2C), 126.8, 125.8, 115.3, 58.0, 51.6, 42.3, 37.4, 32.1 (2C), 28.3. HRMS (ESI) C$_{48}$H$_{63}$N$_8$O$_2$ [M+H]$^+$ calcd=783.5068; found=783.5058.

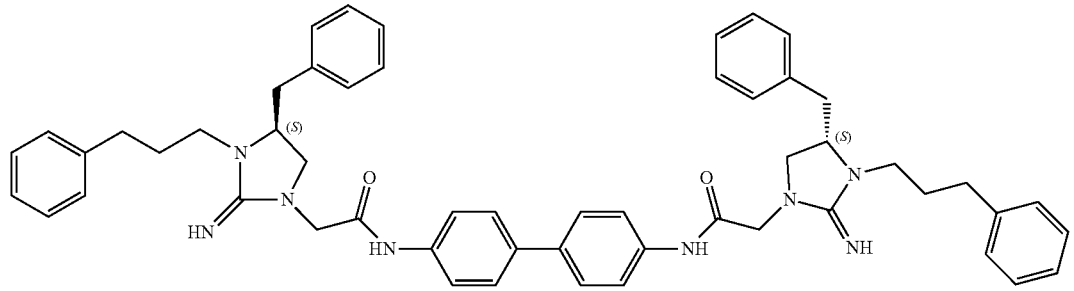

Compound 10

Compound 10. $^1$H NMR (500 MHz, CD$_3$OD) δ 7.64 (d, J=7.5 Hz, 4H), 7.57 (d, J=7.5 Hz, 4H), 7.18-7.33 (m, 20H), 4.22-4.27 (m, 2H), 4.14 (s, 4H), 3.63 (t, J=9.5 Hz, 2H), 3.51-3.57 (m, 2H), 3.42 (dd, J=9.5, 5.0 Hz, 2H), 3.34 (dd, J=9.0, 5.5 Hz, 2H), 3.09 (dd, J=13.5, 4.5 Hz, 2H), 2.85 (dd, J=14.0, 8.5 Hz, 2H), 2.62-2.74 (m, 4H), 1.92-2.06 (m, 4H). $^{13}$C NMR (125 MHz, CD$_3$OD) δ 165.1, 158.0, 140.9, 137.2, 136.2, 135.7, 134.3, 129.0 (2C), 128.5 (2C), 128.2 (2C), 128.0 (2C), 126.8, 126.6 (2C), 125.8, 119.8, 58.0, 51.7, 42.3, 37.4, 32.1 (2C), 28.3. HRMS (ESI) C$_{54}$H$_{59}$N$_8$O$_2$ [M+H]$^+$ calcd=851.4755; found=851.4742.

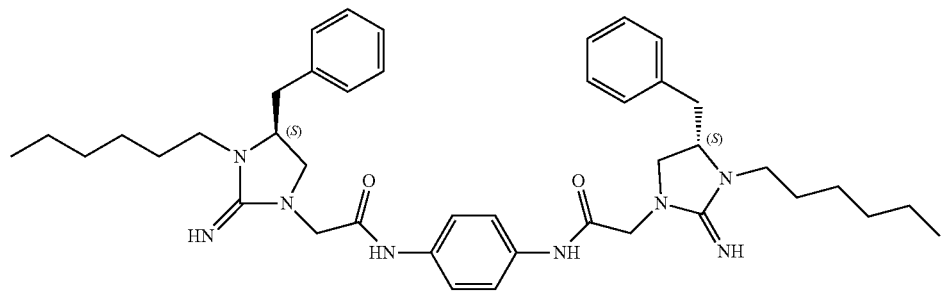

Compound 11

Compound 11. $^1$H NMR (600 MHz, CD$_3$OD) δ 7.50 (brs, 4H), 7.29-7.32 (m, 4H), 7.22-7.26 (m, 6H), 4.26-4.31 (m, 2H), 4.08 (s, 4H), 3.65 (t, J=9.6 Hz, 2H), 3.45 (ddd, J=15.0, 9.0, 6.6 Hz, 2H), 3.40 (dd, J=9.6, 5.4 Hz, 2H), 3.24-3.27 (m, 2H), 3.14 (dd, J=13.8, 4.8 Hz, 2H), 2.87 (dd, J=13.2, 8.4 Hz, 2H), 1.58-1.69 (m, 4H), 1.32-1.37 (m, 16H), 0.91 (t, J=7.2 Hz, 6H). $^{13}$C NMR (150 MHz, CD$_3$OD) δ 165.0, 158.0, 135.8, 134.3, 129.0 (2C), 128.4 (2C), 126.7, 120.0 (2C), 57.9, 51.7, 42.8, 37.5, 31.1, 26.6, 25.8, 22.1, 12.9. HRMS (ESI) C$_{42}$H$_{59}$N$_8$O$_2$ [M+H]$^+$ calcd=707.4755; found=707.4748.

Compound 12

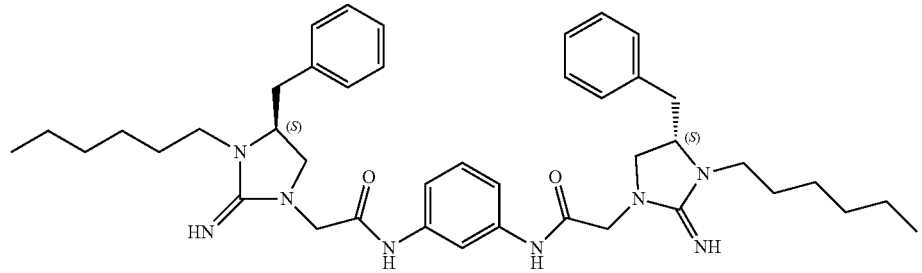

Compound 12. $^1$H NMR (500 MHz, CD$_3$OD) δ 8.05 (s, 1H), 7.31-7.34 (m, 4H), 7.24-7.28 (m, 9H), 4.27-4.32 (m, 2H), 4.14, 4.10 (ABq, J=18.0 Hz, 4H), 3.65 (t, J=8.0 Hz, 2H), 3.47 (ddd, J=15.0, 9.0, 6.5 Hz, 2H), 3.42 (dd, J=9.5, 5.5 Hz, 2H), 3.24-3.27 (m, 2H), 3.16 (dd, J=13.5, 5.0 Hz, 2H), 2.89 (dd, J=13.5, 8.0 Hz, 2H), 1.59-1.69 (m, 4H), 1.32-1.37 (m, 12H), 0.92 (t, J=7.0 Hz, 6H). $^{13}$C NMR (125 MHz, CD$_3$OD) δ 165.2, 158.0, 138.5, 135.8, 129.0 (2C), 128.5 (2C), 126.8, 115.3, 111.1, 62.9, 58.0, 42.9, 37.5, 31.1, 26.6, 25.8, 22.1, 12.9. HRMS (ESI) C$_{42}$H$_{59}$N$_8$O$_2$ [M+H]$^+$ calcd=707.4755; found=707.4751.

Compound 13

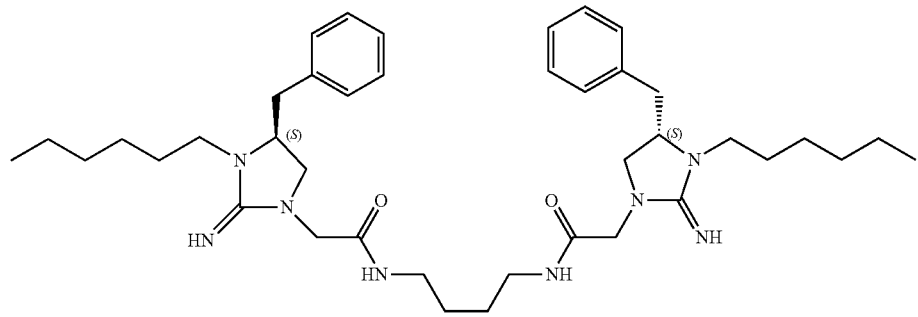

Compound 13. $^1$H NMR (500 MHz, CD$_3$OD) δ 7.30-7.34 (m, 4H), 7.24-7.26 (m, 6H), 4.24-4.30 (m, 2H), 3.94, 3.90 (ABq, J=18.0 Hz, 4H), 3.59 (t, J=9.5 Hz, 2H), 3.45 (ddd, J=15.0, 9.0, 6.5 Hz, 2H), 3.34 (dd, J=9.5, 6.0 Hz, 2H), 3.23-3.29 (m, 2H), 3.19-3.23 (m, 4H), 3.13 (dd, J=13.5, 5.0 Hz, 2H), 2.87 (dd, J=14.0, 8.0 Hz, 2H), 1.51-1.54 (m, 4H), 1.28-1.36 (m, 12H), 0.92 (t, J=6.5 Hz, 6H). $^{13}$C NMR (125 MHz, CD$_3$OD) δ 167.0, 157.9, 135.8, 129.0 (2C), 128.5 (2C), 126.8, 57.9, 51.6, 46.7, 42.9, 38.7, 37.5, 31.1, 26.6, 26.2, 25.8, 22.1, 12.9. HRMS (ESI) C$_{40}$H$_{63}$N$_8$O$_2$ [M+H]$^+$ calcd=687.5068; found=687.5056.

Compound 14

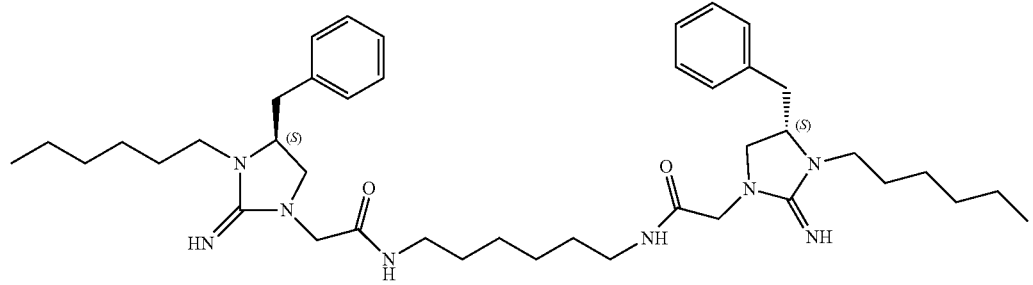

Compound 14. $^1$H NMR (600 MHz, CD$_3$OD) δ 7.30-7.32 (m, 4H), 7.22-7.25 (m, 6H), 4.23-4.27 (m, 2H), 3.91, 3.87 (ABq, J=17.4 Hz, 4H), 3.57 (t, J=9.6 Hz, 2H), 3.43 (ddd, J=15.0, 9.6, 6.6 Hz, 2H), 3.32 (dd, J=9.0, 5.4 Hz, 2H), 3.21-3.26 (m, 2H), 3.17 (t, J=7.2 Hz, 4H), 3.12 (dd, J=13.8, 4.8 Hz, 2H), 2.83 (dd, J=13.8, 7.8 Hz, 2H), 1.57-1.64 (m, 4H), 1.48 (t, J=6.6 Hz, 4H), 1.26-1.34 (m, 20H), 0.89 (t, J=7.2 Hz, 6H). $^{13}$C NMR (150 MHz, CD$_3$OD) δ 166.9, 157.9, 135.8, 128.9 (2C), 128.4 (2C), 126.8, 57.9, 51.5, 46.6, 42.9, 39.0, 37.5, 31.1, 28.0, 26.6, 26.1, 25.8, 22.1, 12.9. HRMS (ESI) C$_{42}$H$_{67}$N$_8$O$_2$ [M+H]$^+$ calcd=715.5381; found=715.5371.

Compound 15

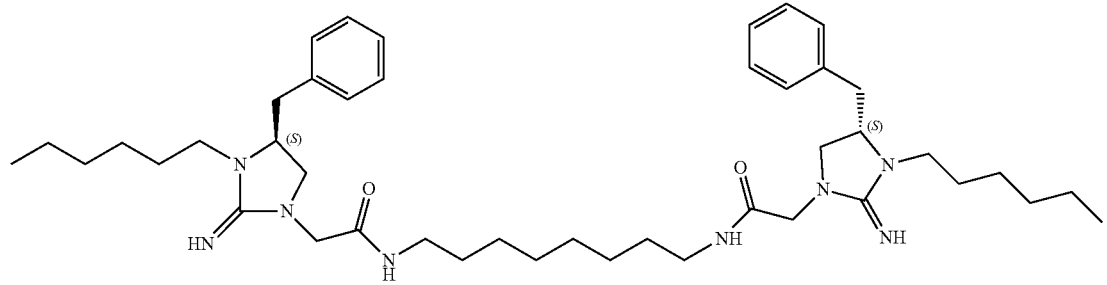

Compound 15. $^1$H NMR (500 MHz, CD$_3$OD) δ 7.31-7.34 (m, 4H), 7.24-7.27 (m, 6H), 4.24-4.30 (m, 2H), 3.94, 3.90 (ABq, J=18.0 Hz, 4H), 3.59 (t, J=9.0 Hz, 2H), 3.45 (ddd, J=15.0, 9.0, 6.5 Hz, 2H), 3.34 (dd, J=9.5, 5.5 Hz, 2H), 3.25 (ddd, J=15.0, 9.0, 5.5 Hz, 2H), 3.18 (t, J=7.0 Hz, 4H), 3.14 (dd, J=13.5, 5.0 Hz, 2H), 2.86 (dd, J=13.5, 8.0 Hz, 2H), 1.54-1.69 (m, 4H), 1.50 (t, J=6.0 Hz, 4H), 1.30-1.36 (m, 20H), 0.92 (t, J=7.0 Hz, 6H). $^{13}$C NMR (125 MHz, CD$_3$OD) δ 166.9, 157.9, 135.8, 128.9 (2C), 128.5 (2C), 126.8, 57.9, 51.5, 46.7, 42.8, 39.2, 37.5, 31.2, 28.9, 26.6, 26.5, 25.8, 22.2, 12.9. HRMS (ESI) C$_{44}$H$_{71}$N$_8$O$_2$ [M+H]$^+$ calcd=743.5694; found=743.5675.

Compound 16

Compound 16. $^1$H NMR (500 MHz, CD$_3$OD) δ 7.30-7.34 (m, 4H), 7.24-7.27 (m, 6H), 4.25-4.30 (m, 2H), 3.93, 3.89 (ABq, J=17.5 Hz, 4H), 3.55-3.63 (m, 8H), 3.50 (t, J=6.5 Hz, 3H), 3.45 (ddd, J=18.5, 9.5, 6.5 Hz, 2H), 3.34 (dd, J=9.5, 6.6 Hz, 2H), 3.23-3.28 (m, 4H), 3.14 (dd, J=13.5, 5.0 Hz, 2H), 2.86 (dd, J=13.5, 8.0 Hz, 2H), 1.76 (quintet, J=6.5 Hz, 4H), 1.55-1.69 (m, 4H), 1.31-1.37 (m, 12H), 0.92 (t, J=6.0 Hz, 6H). $^{13}$C NMR (125 MHz, CD$_3$OD) δ 166.9, 157.9, 135.8, 129.0 (2C), 128.5 (2C), 126.8, 70.0, 69.8, 68.3, 57.9, 51.6, 46.7, 42.9, 37.5, 36.7, 31.9, 31.1, 28.9, 26.6, 25.8, 22.1, 12.9. HRMS (ESI) C$_{46}$H$_{75}$N$_8$O$_5$ [M+H]$^+$ calcd=819.5855; found=819.5845.

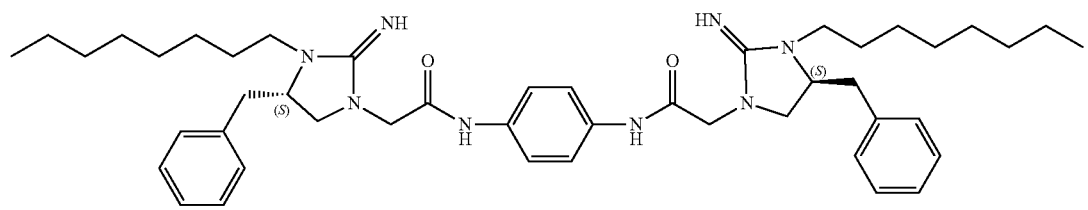

Compound 17

Compound 17. $^1$H NMR (500 MHz, CD$_3$OD) δ 8.02 (d, J=1.0 Hz, 1H), 7.31-7.34 (m, 4H), 7.24-7.28 (m, 9H), 4.27-4.32 (m, 2H), 4.14, 4.11 (ABq, J=18.0 Hz, 4H), 3.67 (t, J=9.5 Hz, 2H), 3.47 (ddd, J=15.5, 9.5, 7.0 Hz, 2H), 3.42 (dd, J=9.5, 5.5 Hz, 2H), 3.27 (ddd, J=15.0, 9.5, 5.5 Hz, 2H), 3.16 (dd, J=13.5, 5.0 Hz, 2H), 2.89 (dd, J=14.9, 8.5 Hz, 2H), 1.59-1.70 (m, 4H), 1.30-1.34 (m, 20H), 0.91 (t, J=7.0 Hz, 6H). $^{13}$C NMR (125 MHz, CD$_3$OD) δ 165.2, 158.0, 138.6, 135.8, 129.0 (2C), 128.5 (2C), 126.8, 115.3, 111.2, 58.0, 51.7, 42.8, 37.5, 31.5, 28.9 (2C), 26.7, 26.1, 22.3, 13.0. HRMS (ESI) C$_{46}$H$_{67}$N$_8$O$_2$ [M+H]$^+$ calcd=763.5381; found=763.5359.

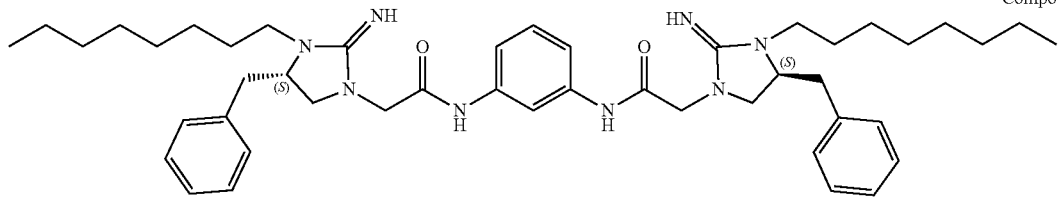

Compound 18

Compound 18. $^1$H NMR (500 MHz, CD$_3$OD) δ 7.52 (s, 4H), 7.31-7.34 (m, 4H), 7.24-7.28 (m, 6H), 4.27-4.33 (m, 2H), 4.12, 4.09 (ABq, J=18.5 Hz, 4H), 3.67 (t, J=9.5 Hz, 2H), 3.48 (ddd, J=15.5, 9.0, 7.0 Hz, 2H), 3.42 (dd, J=9.5, 5.5 Hz, 2H), 3.25-3.29 (m, 2H), 3.16 (dd, J=14.0, 5.0 Hz, 2H), 2.89 (dd, J=13.5, 8.5 Hz, 2H), 1.58-1.71 (m, 4H), 1.27-1.35 (m, 20H), 0.91 (t, J=6.5 Hz, 6H). $^{13}$C NMR (125 MHz, CD$_3$OD) δ 165.0, 158.0, 135.8, 134.3, 129.0 (2C), 128.5 (2C), 126.7, 120.0 (2C), 57.9, 51.7, 47.0, 42.8, 37.5, 31.5, 28.9 (2C), 26.6, 26.0, 22.3, 13.0. HRMS (ESI) C$_{46}$H$_{67}$N$_8$O$_2$ [M+H]$^+$ calcd=763.5381; found=763.5358.

Compound 19

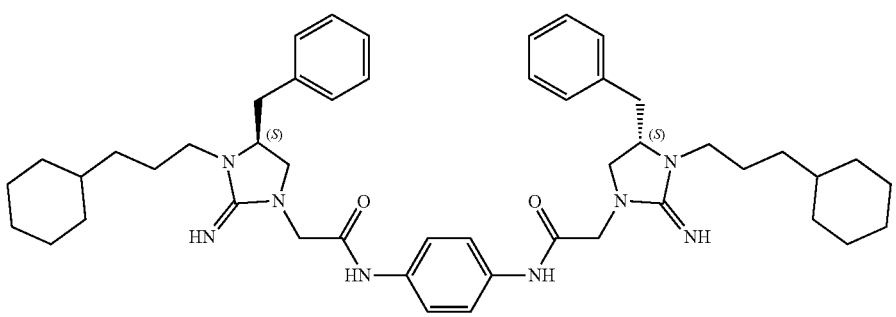

Compound 19. ¹H NMR (500 MHz, CD$_3$OD) δ 7.53 (s, 4H), 7.31-7.34 (m, 4H), 7.24-7.28 (m, 6H), 4.27-4.32 (m, 2H), 4.13, 4.10 (ABq, J=18.0 Hz, 4H), 3.68 (t, J=9.0 Hz, 2H), 3.41-3.48 (m, 4H), 3.25 (ddd, J=15.0, 9.5, 5.5 Hz, 2H), 3.15 (dd, J=13.5, 5.0 Hz, 2H), 2.89 (dd, J=13.5, 8.0 Hz, 2H), 1.58-1.76 (m, 14H), 1.15-1.32 (m, 12H), 0.90-0.97 (m, 4H). ¹³C NMR (125 MHz, CD$_3$OD) δ 165.1, 158.0, 135.8, 134.3, 128.9 (2C), 128.5 (2C), 126.8, 120.1 (2C), 57.9, 51.8, 47.0, 43.1, 37.6, 37.5, 37.3, 33.6, 33.0, 32.9, 26.3, 26.0, 24.0. HRMS (ESI) C$_{48}$H$_{67}$N$_8$O$_2$ [M+H]$^+$ calcd=787.5381; found=787.5374.

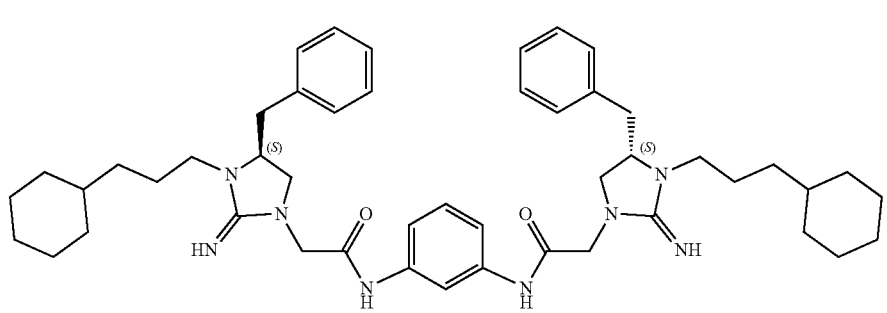

Compound 20

Compound 20. ¹H NMR (500 MHz, CD$_3$OD) δ 8.04 (s, 1H), 7.31-7.34 (m, 4H), 7.24-7.28 (m, 9H), 4.26-4.32 (m, 2H), 4.14, 4.10 (ABq, J=18.0 Hz, 4H), 3.68 (t, J=9.5 Hz, 2H), 3.41-3.47 (m, 4H), 3.25 (ddd, J=14.5, 9.0, 5.5 Hz, 2H), 3.15 (dd, J=13.5, 5.0 Hz, 2H), 2.89 (dd, J=13.5, 8.0 Hz, 2H), 1.60-1.75 (m, 14H), 1.14-1.32 (m, 12H), 0.90-0.96 (m, 4H). ¹³C NMR (125 MHz, CD$_3$OD) δ 165.2, 158.0, 138.6, 135.8, 128.9 (2C), 128.5 (2C), 126.8, 120.1 115.3, 58.0, 51.7, 47.0, 43.1, 37.6, 37.3, 33.7, 33.0, 32.9, 26.3, 26.0 (2C), 24.0. HRMS (ESI) C$_{48}$H$_{67}$N$_8$O$_2$ [M+H]$^+$ calcd=787.5381; found=787.5357.

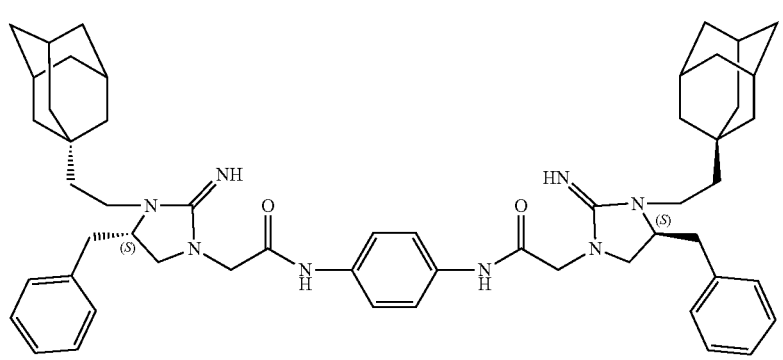

Compound 21

Compound 21. ¹H NMR (500 MHz, CD$_3$OD) δ 7.53 (s, 4H), 7.32-7.35 (m, 4H), 7.25-7.29 (m, 6H), 4.28-4.34 (m, 2H), 4.13 (s, 4H), 3.69 (t, J=9.5 Hz, 2H), 3.51-3.57 (m, 2H), 3.42 (dd, J=10.0, 5.5 Hz, 2H), 3.15-3.20 (m, 2H), 3.12 (dd, J=13.5, 5.5 Hz, 2H), 2.90 (dd, J=14.0, 8.0 Hz, 2H), 1.95 (brs, 6H), 1.67-1.77 (m, 12H), 1.52-1.54 (m, 10H), 1.44 (td, J=13.0, 4.5 Hz, 2H), 1.33-1.47 (m, 4H). ¹³C NMR (125 MHz, CD$_3$OD) δ 165.0, 158.0, 136.0, 134.3, 129.0 (2C), 128.5 (2C), 126.8, 120.0 (2C), 57.4, 51.9, 41.7, 41.6 (2C), 39.6, 38.1, 38.0, 36.6 (2C), 31.2, 28.6 (2C), 28.6. HRMS (ESI) C$_{54}$H$_{71}$N$_8$O$_2$ [M+H]$^+$ calcd=863.5694; found=863.5665.

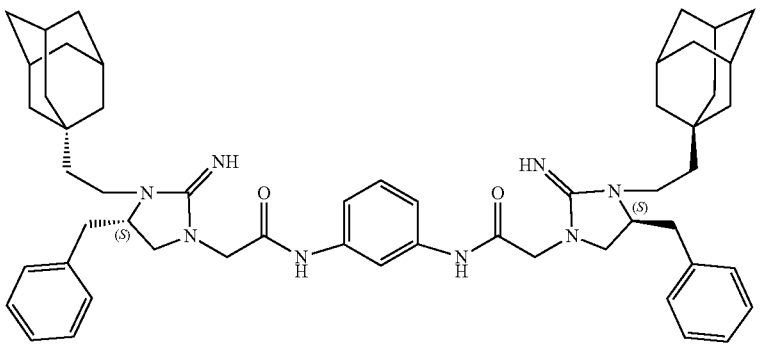

Compound 22

Compound 22. $^1$H NMR (500 MHz, CD$_3$OD) δ 8.12 (t, J=1.5 Hz, 1H), 7.34 (t, J=7.5 Hz, 4H), 7.22-7.29 (m, 9H), 4.28-4.33 (m, 2H), 4.15, 4.12 (ABq, J=18.5 Hz, 4H), 3.70 (t, J=9.5 Hz, 2H), 3.53 (qd, J=7.0, 5.5 Hz, 2H), 3.42 (dd, J=10.0, 5.5 Hz, 2H), 3.16-3.19 (m, 2H), 3.12 (dd, J=14.0, 5.5 Hz, 2H), 2.90 (dd, J=14.0, 7.5 Hz, 2H), 1.95 (brs, 6H), 1.67-1.77 (m, 12H), 1.52-1.54 (m, 12H), 1.44 (td, J=13.0, 4.5 Hz, 2H), 1.35 (td, J=12.0, 5.5 Hz, 2H). $^{13}$C NMR (125 MHz, CD$_3$OD) δ 165.2, 158.0, 138.6, 136.0, 129.0 (2C), 128.5 (3C), 126.8, 115.3, 111.2, 57.4, 51.9, 41.7 (3C), 39.6, 38.1, 38.0, 36.6 (2C), 31.3, 28.6 (3C), 28.6. HRMS (ESI) C$_{54}$H$_{71}$N$_8$O$_2$ [M+H]$^+$ calcd=863.5694; found=863.5670.

Building block R5. $^1$H NMR (500 MHz, CD$_3$OD) δ 7.25-7.29 (m, 2H), 7.19-7.21 (m, 3H), 3.73-3.97 (m, 3H), 3.59 (s, 1H), 3.43-3.50 (m, 1H), 2.95-3.11 (m, 2H), 2.77-2.81 (m, 2H), 1.88 (brd, 4H), 1.71 (brd, 4H), 1.60 (brd, 4H), 1.28-1.52 (m, 21H), 0.87-0.92 (m, 3H). $^{13}$C NMR (125 MHz, CD$_3$OD) δ 171.7, 155.8, 155.7, 128.9 (2C), 128.0 (2C), 126.0, 80.5, 80.3, 79.5, 79.2, 49.3, 42.0 (3C), 41.8, 36.8 (3C), 36.5, 31.2, 28.6 (4C), 28.5, 27.6, 27.5 (2C), 27.4, 27.3, 27.2. HRMS (ESI) C$_{33}$H$_{51}$N$_2$O$_6$ [M+H]$^+$ calcd=571.3742; found=571.3763.

Compound 23

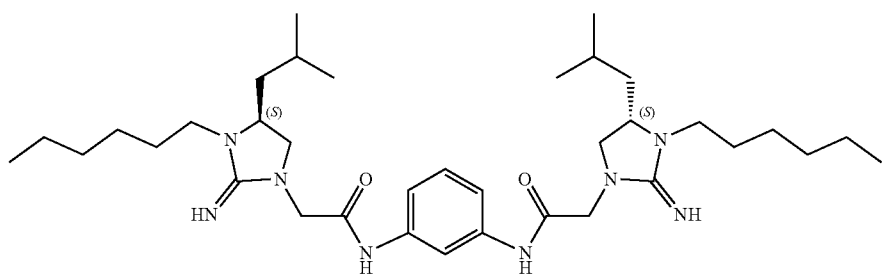

Compound 23. $^1$H NMR (500 MHz, CD$_3$OD) δ 8.03 (dd, J=3.0, 1.5 Hz, 1H), 7.25-7.30 (m, 3H), 4.29, 4.22 (ABq, J=18.0 Hz, 4H), 4.04 (qd, J=9.5, 3.0 Hz, 2H), 3.84 (t, J=9.5 Hz, 2H), 3.41 (ddd, J=15.0, 9.0, 6.5 Hz, 2H), 3.37 (t, J=7.5 Hz, 2H), 3.27 (ddd, J=14.5, 9.0, 5.5 Hz, 2H), 1.64-1.74 (m, 6H), 1.50-1.60 (m, 4H), 1.32-1.39 (m, 12H), 0.99 (d, J=6.5 Hz, 6H), 0.96 (d, J=6.5 Hz, 6H), 0.93 (t, J=7.0 Hz, 6H). $^{13}$C NMR (125 MHz, CD$_3$OD) δ 165.2, 158.2, 138.6, 128.9, 115.3, 111.1, 55.8, 52.6, 42.3, 40.4, 31.2, 26.5, 25.8, 24.4, 22.7, 22.1, 20.3, 12.9. HRMS (ESI) C$_{36}$H$_{63}$N$_8$O$_2$ [M+H]$^+$ calcd=639.5068; found=639.5046.

R5

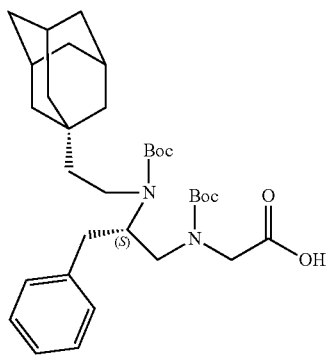

Example 2. Antibacterial Activity

Minimum Inhibitory Concentrations (MICs) Against Bacteria.

The antimicrobial activity of the compounds was tested on the following six bacteria strains: *K. pneumoniae* (ATCC 13383), *P. aeruginosa* (ATCC27853), *E. coli* (ATCC 25922), vancomycin-resistant *Enterococcus faecalis* (ATCC 700802), Methicillin-resistant *S. aureus* (MRSA, ATCC 33591), Methicillin-resistant *S. epidermidis* (MRSE, RP62A). The procedures were followed as reported previously (Hancock et al., *Immunobiology* 2006, 211, 315-322). Briefly, a single colony of each bacterium was inoculated in 3 mL TSB medium and incubated overnight at 37° C. Then the bacteria culture was diluted at 1:100 and the bacteria were allowed to grow to mid-logarithmic phase. Next, 50 μL of 2-fold serial dilutions of compounds (0.1-25 μg/mL) were added the 96-well plate containing aliquots of 50 μL of bacteria suspension (1×10$^6$ CFU/mL) in each well. The mixture was incubated at 37° C. for 16 h, and their absorption at 600 nm wavelength was read on a Biotek Synergy HT microtiter plate reader. The MICs were determined as the lowest concentration that completely inhibits the bacteria growth. The experiments were repeated at least three times with duplicates each time. HC$_{50}$ means the concentration causing 50% hemolysis.

Hemolytic Assays.

The freshly drawn, K2EDTA treated human red blood cells (hRBCs) were washed with 1×PBS buffer, and centrifuged at 3500 rpm for 10 min. The step was repeated until the supernatant became clear. The supernatant was removed, and the RBCs were diluted into 5% v/v suspension. 50 μL of the suspension was incubated with 50 μL of compounds of different concentrations at 37° C. for 1 h. The mixture was centrifuged at 3500 rpm for 10 min. Subsequently, to 30 μL of the supernatant 100 μL PBS was added, and the absorbance of the mixture at 540 nm was read on a Biotek Synergy HT plate reader. The positive control was 2% Triton X-100, and the negative control was 1×PBS alone. The hemolysis activity was calculated by the formula % hemolysis=$(Abs_{sample}-Abs_{PBS})/(Abs_{Triton}-Abs_{PBS}) \times 100\%$. The experiment was repeated at least three times with duplicates each time. Hemolysis activity was not measured for peptidomimetics that did not exhibit antimicrobial activity.

Daptomycin and colistin, which are last-resort antibiotics and active against either Gram-positive or Gram-negative bacteria, were included for comparison. The antibacterial activities of compounds 1-10 are shown in Table 1.

better span the phospholipid bilayer, both 5 and 6 displayed remarkable antibacterial activity with MICs less than 3.0 μg/mL for Gram-negative bacteria (except for *P. aeruginosa*), and less than 3.0 μg/mL against Gram-positive bacteria. In particular, the MIC of compound 5 was as potent as 0.33 μg/mL, which is better or at least comparable to any known bis-cyclic guanidine compounds. It also seemed p-phenylene and m-phenylene spacers do not impact activity intensively, as 3 and 4, and 5 and 6 exhibited similar activities. However, compound 6 ($HC_{50}$>250 μg/mL) with m-phenylene spacer is less hemolytic than compound 5 ($HC_{50}$=140 μg/mL) with p-phenylene spacer. Further, monomeric compounds 7 and 8 only displayed negligible activity, possibly due to insufficient interaction with bacterial membranes. It was also noted that compound 9 bearing the aliphatic $C_6H_{12}$ spacer showed comparable activity with 6 but was not active against *P. aeruginosa*, and was even more hemolytic ($HC_{50}$=100 g/mL), suggesting that the rigidity of the linker plays a role in the activity. In addition, the conformation of the linker also seemed to affect the antibacterial activity. For instance, compound 10 bearing a biphenyl linker was not active against the bacteria tested

TABLE 1

| | MIC (μg/mL) | | | | | | | |
|---|---|---|---|---|---|---|---|---|
| | Gram − | | | Gram + | | | Hemolysis | |
| Compounds | E. coli | P. aeruginosa | K. pneumoniae | MRSA | MRSE | VRE | ($HC_{50}$, μg/mL) | Activity Index** |
| 1 | >25 | ND* | ND | >25 | ND | ND | ND | ND |
| 2 | >25 | ND | ND | >25 | ND | ND | ND | ND |
| 3 | 1.5 | >25 | >25 | 6~12 | >25 | >25 | ND | ND |
| 4 | 3.0 | >25 | >25 | 6~12 | >25 | >25 | ND | ND |
| 5 | 1.5~3 | 12~25 | 1.5~3 | 0.33 | 0.75 | 0.75 | 140 | 424 |
| 6 | 3~6 | 12~25 | 3.0 | 1.5~3 | 1.5 | 1.5 | >250 | >83 |
| 7 | >25 | ND | ND | 12~25 | ND | ND | ND | ND |
| 8 | >25 | ND | ND | 12~25 | ND | ND | ND | ND |
| 9 | 3~6 | >25 | 3~6 | 0.75 | 0.75~1.5 | 1.5~3 | 100 | 66 |
| 10 | >25 | ND | ND | >25 | ND | ND | ND | ND |
| Daptomycin | >50 | >50 | >50 | 0.5 | 0.5 | 1.0 | | |
| Colistin | 0.5 | 1.0 | 0.5 | >50 | >50 | >50 | | |

*ND, Not determined because compounds are not active.
**Activity Index, determined by $HC_{50}/MIC_{MRSA}$.

Compounds 3 and 4 showed excellent activity against Gram-negative bacteria *E. coli* with MICs of 1.5 and 3 μg/mL, respectively. In addition, these compounds also exhibited activity toward MRSA (6-12 μg/mL). Replacement of ethyl group in 3 and 4 with the 3-phenylpropyl group led to compounds 5 and 6, respectively. With more hydrophobic and longer chains which were expected to herein. Without being bound by any theory, this could be attributed to the twisted nature of two phenyl rings in the biphenyl linker, which prevented the whole molecule to adopt the flat conformation, leading to weakened efficiency to bind with the outer layer of bacteria.

The antibacterial activities of compounds 11-23 are shown in Table 2.

TABLE 2

| | MIC (μg/mL) | | | | | | | |
|---|---|---|---|---|---|---|---|---|
| | Gram − | | | Gram + | | | Hemolysis | |
| Compounds | E. coli | P. aeruginosa | K. pneumoniae | MRSA | MRSE | VRE | ($HC_{50}$, μg/mL) | Activity Index |
| 11 | 1.5 | 6 | 1.5 | 0.33 | 0.75 | 0.75 | >250 | >769 |
| 12 | 0.75 | 4 | 0.75 | 0.16 | 0.75 | 0.75 | >250 | >1534 |
| 13 | 1.5 | >25 | 6~12 | 0.75 | 1.5 | 3~6 | >250 | >333 |
| 14 | 1.5 | >25 | 3~6 | 0.325 | 0.75 | 1.5 | >250 | >769 |
| 15 | 0.75~1.5 | >25 | 1.5~3 | 0.75 | 1.5 | 0.325 | >250 | >333 |
| 16 | 1.5~3 | >25 | >25 | 0.75 | 1.5 | 6~12 | 200 | 267 |
| 17 | >25 | ND | ND | 1.5 | ND | ND | ND | ND |
| 18 | >25 | ND | ND | 1.5 | ND | ND | ND | ND |

TABLE 2-continued

| | MIC (μg/mL) | | | | | | Hemolysis | |
| --- | --- | --- | --- | --- | --- | --- | --- | --- |
| | Gram − | | | Gram + | | | (HC$_{50}$, | Activity |
| Compounds | E. coli | P. aeruginosa | K. pneumoniae | MRSA | MRSE | VRE | μg/mL) | Index |
| 19 | 12 | >25 | 1.5~3 | 0.75 | 0.33 | 0.75 | 5 | 6 |
| 20 | 12 | >25 | 1.5~3 | 0.325 | 0.33 | 1.5 | 26 | 80 |
| 21 | >25 | ND | ND | 6.0 | ND | ND | ND | ND |
| 22 | >25 | ND | ND | 3.0 | ND | ND | ND | ND |
| 23 | 1.5~3 | 6~12 | 0.75 | 1.5 | 1.5 | 0.75 | 200 | 266 |
| Daptomycin | >50 | >50 | >50 | 0.5 | 0.5 | 1.0 | | |
| Colistin | 0.5 | 1.0 | 0.5 | >50 | >50 | >50 | | |

The subsequent studies revealed that the aliphatic chain $C_6H_{13}$ as the $R_2$ group could further enhance the antimicrobial activity. Both compounds 11 and 12 exhibited potent and broad-spectrum activity against all tested bacterial strains. In particular, compound 12 had remarkable MICs of 0.75 μg/mL toward most strains, and MIC of 0.16 μg/mL against MRSA. In addition, both compounds 11 and 12 were very selective, as their hemolytic activity are all more than 250 μg/mL, which demonstrated 769 and 1534 folds of selectivity against MIC values of MRSA, respectively. It is known that daptomycin and colistin are last-resort antibiotics and active against Gram-positive and Gram-negative bacteria, respectively. Compound 12 had almost same or even better activity against Gram-positive bacteria compared with daptomycin, meanwhile showed comparable activity against Gram-negative bacteria compared with colistin, suggesting its promising therapeutic potential. Consistent with the abovementioned findings, compounds with flexible aliphatic linkers, including $C_4H_8$ (compound 13), $C_6H_{12}$ (compound 14), $C_8H_{16}$ (compound 15), showed similar activity, except for a reduced activity toward P. aeruginosa. It should be noted that all of the compounds with aliphatic chain $C_6H_{13}$ as the $R_2$ group showed small hemolytic activity (HC$_{50}$>250 μg/mL). PEG linker (compound 16), however, resulted in reduced activity, suggesting hydrophobic linkers may be preferred for effective membrane spanning and interaction. Other compounds with hydrophobic $R_2$ groups (compounds 17-22) were also tested. Compounds 17 and 18, bearing longer aliphatic chain ($C_8H_{17}$) as $R_2$ group compared with 11 and 12, exhibited unexpected decreased activity against the tested bacteria. Hydrophobic and bulky 3-cyclohexanepropyl and 2-adamantylethyl groups (19-22) as the R2 group did not yield compounds with more potent and broad-spectrum activity. Compounds 19 and 20 were hemolytic, with HC$_{50}$ of 5 and 26 μg/mL, respectively. Replacement of the phenyl group in compound 12 with isobutyl group led to slightly less effective and somewhat more hemolytic compound 23.

Example 3. Interaction with Bacterial Membranes

Figures 1A, 1B:
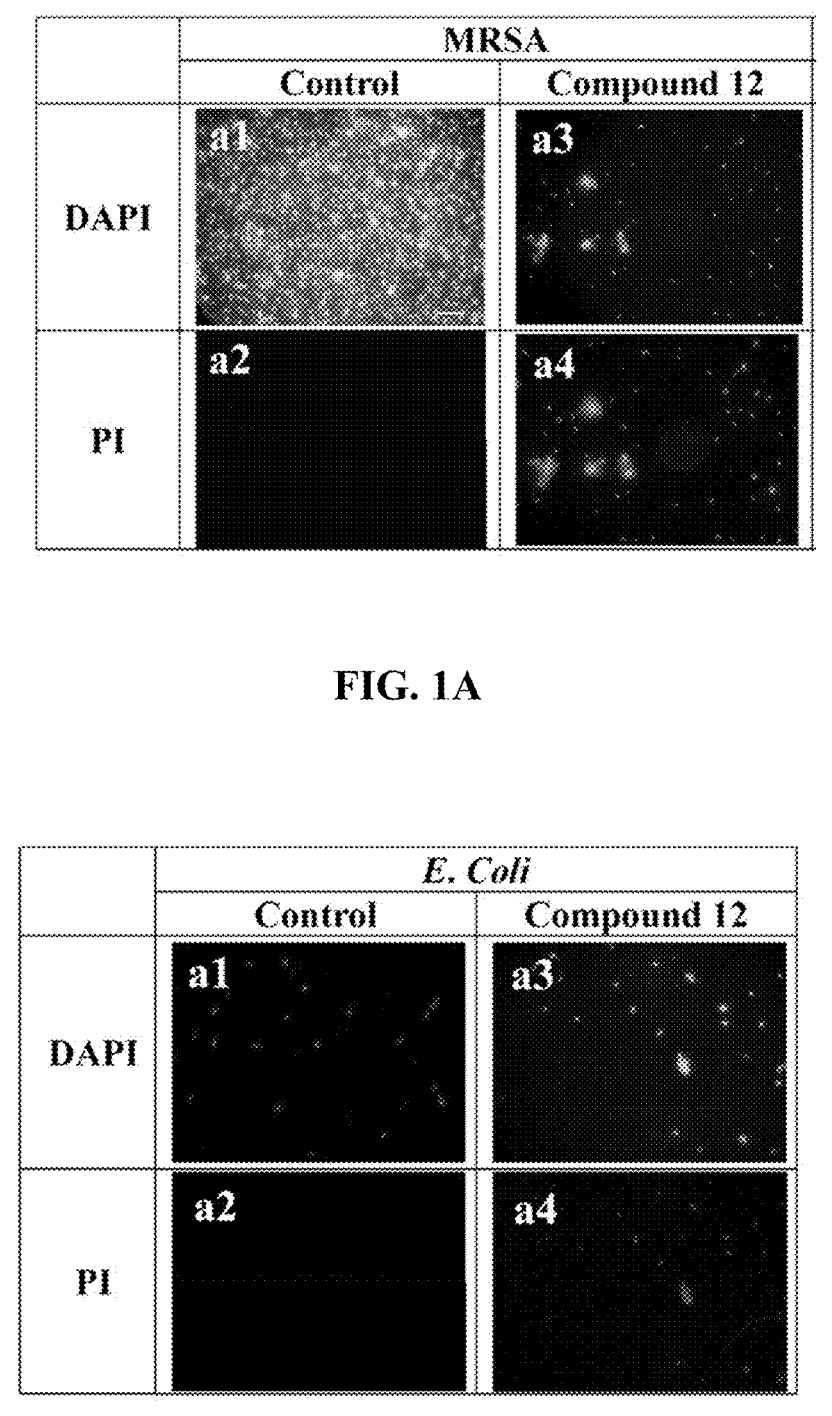

Fluorescence microscopy studies were conducted to evaluate the ability of compound 12 to compromise membranes of S. aureus (Gram-positive bacterium) and E. coli (Gram-negative bacterium). Fluorescent agent 4',6-diamidino-2-phenylindole (DAPI) was used to stain membranes of bacterial cells with blue fluorescence regardless of cell viability, and the red fluorescence of propidium iodide (PI) due to the DNA intercalation was used to stain impaired membranes. After MRSA and E. Coli grew to mid-logarithmic phase, the compound 12 was incubated with the bacteria at 37° C. for 2 h. The mixture was then centrifuged at 5000 rpm for 15 min. The cell pellets were washed with the PBS buffer for three times, and incubated with PI (5 g/mL) and DAPI (10 μg/mL) for 15 min sequentially on ice in the dark. The mixture was then centrifuged and the pellets were washed with the PBS buffer. Next, 10 μL of the samples were placed on chamber slides and observed under Zeiss Axio Image Zloptical microscope using 100× oil-immersion objective. As shown in FIG. 1, treatment of compound 12 gave rise to the red fluorescence under the PI channel in both S. aureus and E. coli groups, indicating that the membranes of these bacteria were disrupted. Moreover, significant aggregation of S. aureus occurred in the presence of compound 12, probably due to the loss of membrane potential upon membrane leakage.

Example 4. Time-Kill Studies

Figure 2B:
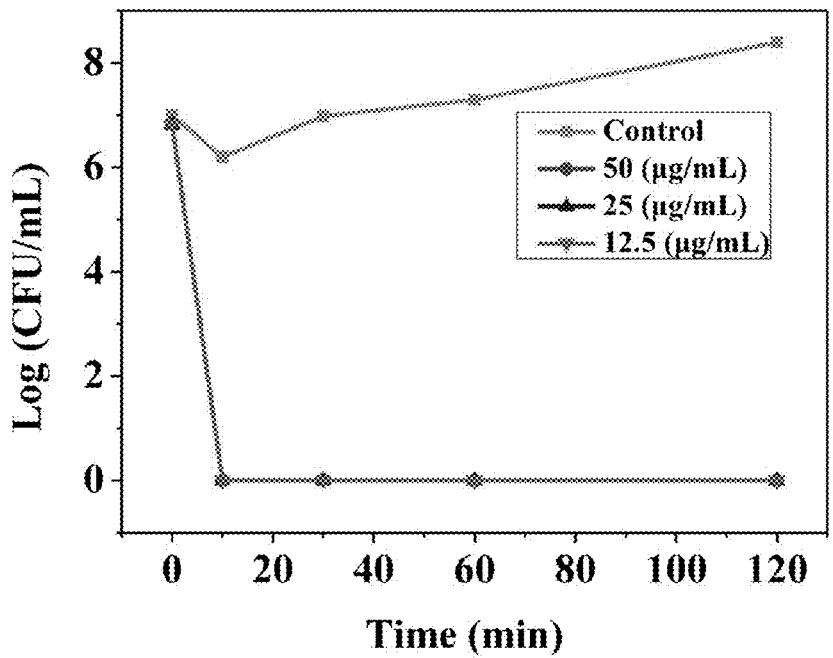

Time-kill studies were conducted to investigate the bacterial killing kinetics of compounds 11 and 12 by using E. Coli. Briefly, the bacteria MRSA grew to mid-logarithmic phase in TSB medium, from which the suspension ($10^6$ CFU/ml) was made. The suspension was incubated with different concentrations of 11 or 12 for 10 min, 30 min, 1 h and 2 h respectively. The mixtures were diluted by $10^2$ to $10^4$ fold and spread on TSB agar plates. After incubation at 37° C. overnight, the colonies on the plates were counted and plotted against the incubation time. As shown in FIG. 2, both compounds killed E. Coli rapidly. Cell colonies were counted in agar plates at 12.5, 25, and 50 μg/mL. Compound 11 at the concentration of 12.5 or 25 μg/mL completely removed all bacteria in 2 hours, and at 50 μg/mL it completely removed bacteria in 0.5 hour. Compound 12 killed E. Coli completely in 0.5 hour at the concentration of 12.5 μg/mL. These data indicate that compounds 11 and 12 contain antibacterial activities similar to that of HDPs.

Example 5. Drug-Resistance Studies

Figure 3:
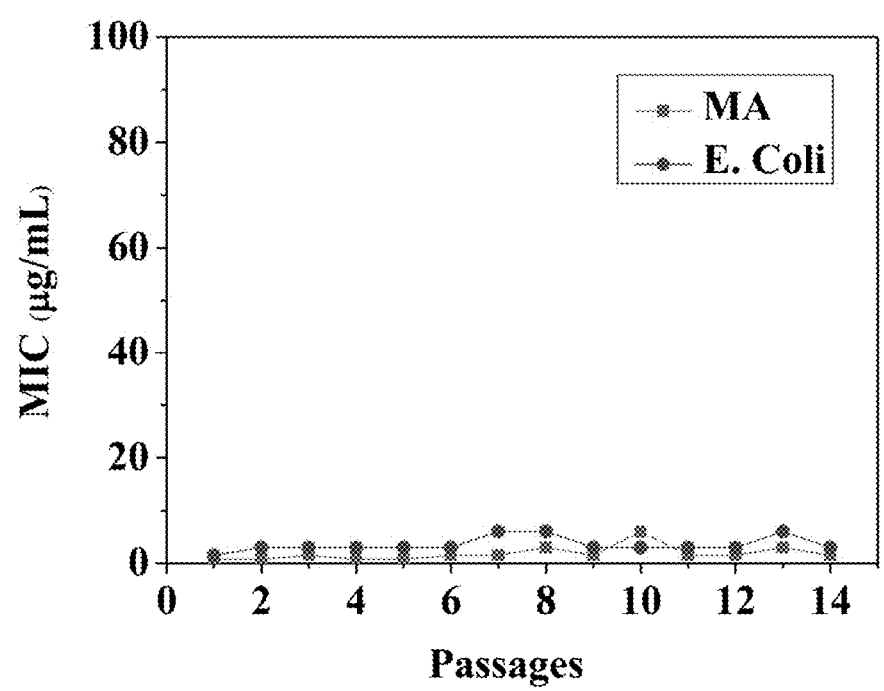
FIG. 3 shows the results of drug-resistance studies of compound 12 toward MRSA and *E. Coli*.

Bacterial resistance tests were conducted using compound 12. The compound was incubated with either MRSA or E. Coli in the well at the concentration of half-MIC (½ MIC, $10^6$ CFU/ml) every day and tested for their activity through 14 successive passages. As shown in FIG. 3, the MICs of compound 12 were virtually constant after 14 passages, indicating that the compound did not readily induce drug resistance in both MRSA and E. Coli. These outcomes suggest that the bis-cyclic guanidine compounds disclosed herein are not vulnerable in developing drug resistance, which is analogous to the mechanism of action of HDPs.

Example 6. Biofilm Inhibition

Bacteria in biofilms are known to tolerate antibiotic treatment and are thus more difficult to eradicate than planktonic cells. Biofilms formed by MRSA and *E. coli* have frustrated the treatment of persistent bacterial infections. Compound 12 was evaluated for its ability to inhibit biofilm formation of MRSA and *E. coli*. Overnight grown bacteria were inoculated into fresh 10% of MHII broth at a ratio of 1:100. 100 µL of inoculated culture was incubated with appropriated amounts of compound 12 in wells of 96-well plate. The plate was incubated at 37° C. for overnight. Optical density of each well was recorded at the wavelength of 600 nm and then the biofilm biomass was recorded by the crystal violet method. Biofilm biomass was presented as CV OD/OD of growth. Relative biofilm biomass values were normalized by the biomass value of control (no addition of compound). Experiments were conducted in triplicate and the data were presented as mean±STDEV.

Figure 4:
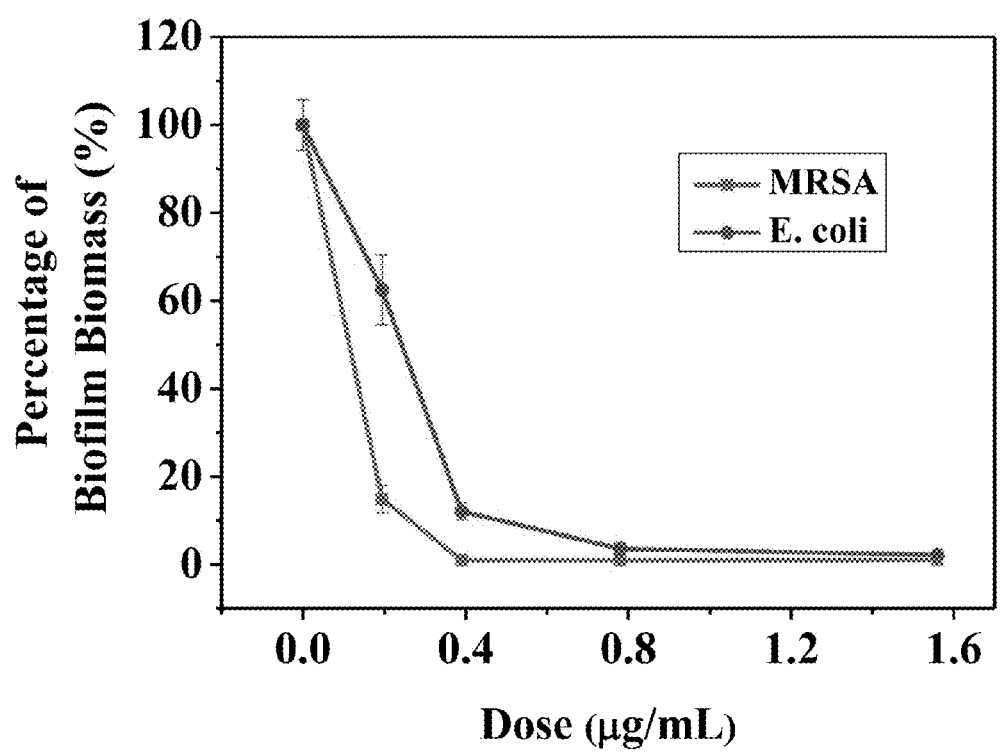
FIG. 4 shows the biological activity of compound 12 on inhibition of biofilm by MRSA and *E. Coli*.

As shown in FIG. 4, compound 12 at 0.19 µg/mL, inhibited 85% of biofilm formation of MRSA and 38% of biofilm formation of *E. coli*. At the concentration of 0.39 µg/mL, compound 12 completely eradicated biofilm formation of MRSA and almost 90% of biofilm formation of *E. coli*. These results reveal that the bis-cyclic guanidine compound is an efficient biofilm formation inhibitor.

Example 7. In Vivo Efficacy

A thigh burden model was employed to evaluate the in vivo anti-infective activity of compounds 11 and 12, in which the thigh muscle of neutropenic mice was inoculated with *S. aureus*, followed by intravenous (i.v.) administration of corresponding compounds. All protocols and methods associated with animal experiments were approved by University of South Florida (USF) Institutional Animal Care and Use Committee. The in vivo experiment on the mouse model of the thigh burden infection with MRSA was conducted adapted from previously reported protocol. The CD-1 female mice which were 6 to 8 weeks old and around 25 g in weights were used for the study. Neutropenic Mice were induced by injecting cyclophosphamide (150 mg/kg) intraperitoneally twice at 4 and 1 days before bacterial inoculation. One MRSA colony from tryptic soy agar (TSA) cultures was allowed to grow in tryptic soy broth (TSB) overnight at 37° C., then 100 µL culture was withdrawn and diluted with TSB to a total volume of 4 mL, which was subsequently incubated at 37° C. for another 6 h. The bacterial culture was then diluted in sterile PBS to give the final inoculum concentration of approximate $10^6$ CFU/mL. The thigh burden infection model was established by injecting both posterior thighs of mice with 100 µL of inoculums. Two doses of the compounds 11 and 12 were given at 1 h and 7 h by i.v. bolus injection in the tail vein at 5 mg/kg per dose of drugs after bacterial infection. Thighs were harvested at 25 h for both groups after bacterial inoculation. Thigh muscles were collected in a sterile tared tube, to which 5 mL sterile PBS was added. The mixture was then homogenized with a tissue homogenizer (BioSpec product tissue tearor 985-370) for approximately 30 sec. 100 mL of serial diluted aliquots were plated on tryptic soy agar plates, which were incubated for 24 h at 37° C. The formed colonies were counted to calculate CFU per thigh.

Figure 5:
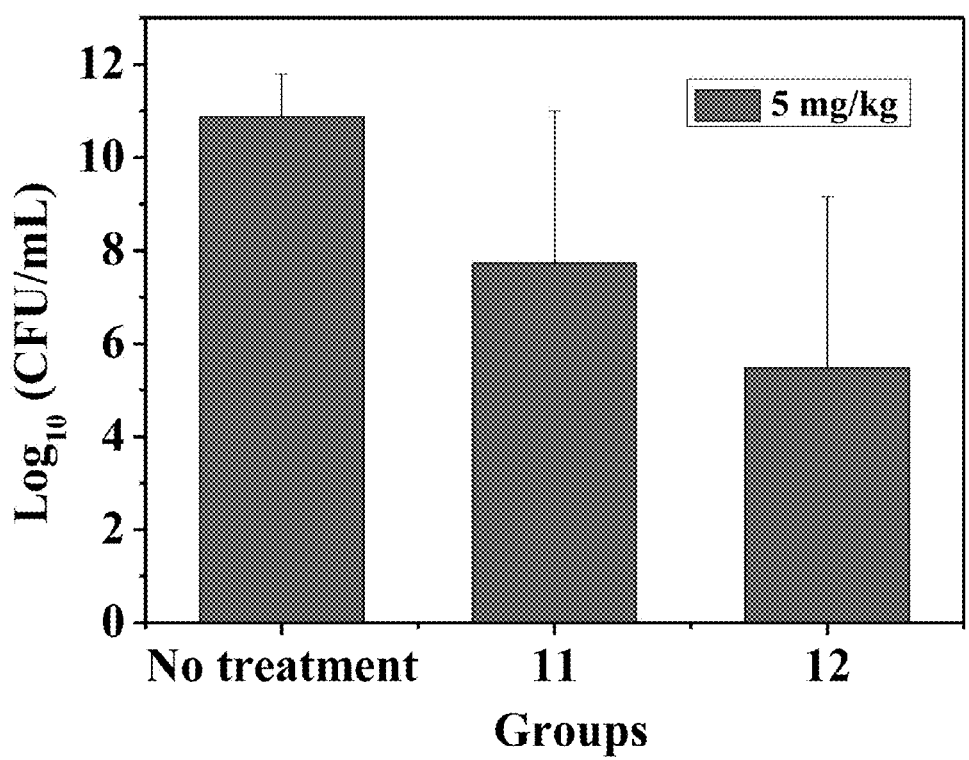
FIG. 5 shows the in vivo efficacy of the compounds 11 and 12 in thigh burden infection model. Neutropenic mice (n=4 per group) were inoculated in the posterior thigh muscles with *S. aureus* ATCC 33591 at 1×10$^6$ CFU per thigh and then treated with compounds 11 and 12 (5 mg/kg per dose) by i.v. bolus injection in the tail vein at 1 and 7 h after infection.

As shown in FIG. 5, significant activity was observed for both compounds at dose of 5 mg/kg when administered twice with a 6-hour interval between injections. A 3-$\log_{10}$ decrease in colony-forming unit (CFU) was observed for compound 11, while a more significant decrease (5-$\log_{10}$ CFU) was observed for compound 12, indicating that compound 12 has better efficacy. The results suggest that the present compounds provided significant protection against infection with *S. aureus*.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

It is also to be understood that the following claims are intended to cover all of the generic and specific features of the invention herein described, and all statements of the scope of the invention that, as a matter of language, might be said to fall therebetween.

For reasons of completeness, various aspects of the invention are set out in the following numbered clauses:

Clause 1. A compound of formula (I), or a salt thereof

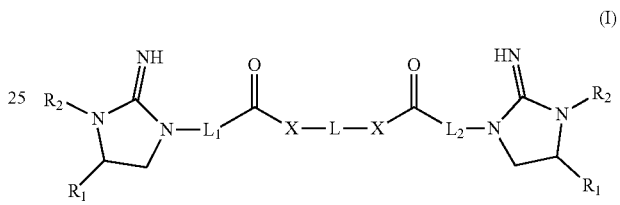

(I)

wherein $R_1$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;

$R_2$ at each occurrence is independently hydrogen, $C_1$-$C_{10}$ alkyl, alkenyl, alkynyl, aryl, aryl-$C_1$-$C_6$ alkyl, cycloalkyl, or cycloalkyl-$C_1$-$C_6$ alkyl;

X is O or NH $L_1$ is $-(CR_xR_y)_{n1}$;

$L_2$ is $-(CR_xR_y)_{n2}$;

L is $-(CR_xR_y)_{n3}-(CH_2CH_2O)_m-G-(CH_2CH_2O)_{m2}-(CR_xR_y)_{n4}-$ $R_x$ and $R_y$ at each occurrence is independently hydrogen or $C_1$-$C_4$ alkyl;

G is a bond or $-(G_1)_t$-, wherein $G_1$ at each occurrence is independently aryl, cycloakyl, heteroaryl, or heterocycle;

n1 and n2 are each independently 1-4;

m1, m2, n3, and n4 are each independently 0-10;

t is 1, 2, 3, or 4; and wherein $R_1$, $R_2$, $R_x$, $R_y$, and $G_1$ optionally are each independently substituted with one or more substituents selected from the group consisting of halogen, cyano, —OH, $C_1$-$C_6$ alkoxy, —COOH, $C_1$-$C_6$ alkoxycarbonyl, oxo, and amino.

Clause 2. The compound of clause 1, or a salt thereof, having a structure of formula (I-a)

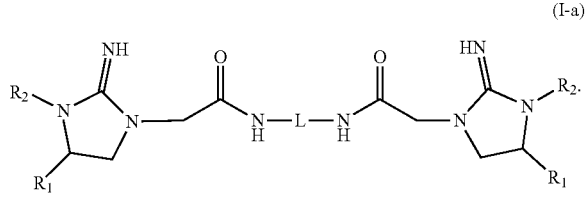

(I-a)

Clause 3. The compound of clause 1 or clause 2, or a salt thereof, wherein L is —(CH$_2$)$_{n3}$— and n3 is 4-8.

Clause 4. The compound of any one of clauses 1-3, or a salt thereof, wherein L is -(G$_1$)$_t$-, and wherein G$_1$ is aryl and t is 1

Clause 5. The compound any one of clauses 1, 2, and 4, or a salt thereof, wherein L is

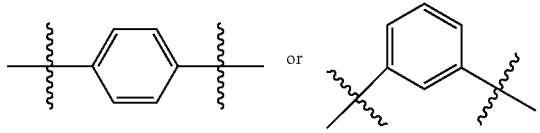

Clause 6. The compound any one of clauses 1-5, or a salt thereof, wherein R$_1$ is C$_1$-C$_{10}$ alkyl or aryl-C$_1$-C$_6$ alkyl Clause 7. The compound any one of clauses 1-6, or a salt thereof, where in R$_1$ is benzyl.

Clause 8. The compound any one of clauses 1-7, or a salt thereof, where in R$_2$ is C$_1$-C$_{10}$ alkyl, aryl-C$_1$-C$_6$ alkyl, or cycloalkyl-C$_1$-C$_6$ alkyl.

Clause 9. The compound any one of clauses 1-8, or a salt thereof, where in R$_2$ is C$_1$-C$_6$ alkyl.

Clause 10. The compound of any one of clauses 1, 2, and 4-9, or a salt thereof, wherein R$_1$ is benzyl, R$_2$ is C$_1$-C$_6$ alkyl, and L is

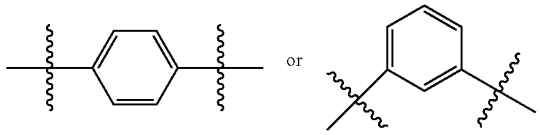

Clause 11. A pharmaceutical composition comprising at least one pharmaceutically acceptable carrier and an effective amount of a compound of any one of clauses 1-10, or a salt thereof.

Clause 12. A method of treating infection in a subject in need thereof, the method comprising administering to the subject an effective amount of a compound of any one of clauses 1-10, or a salt thereof.

Clause 13. The method of clause 12, wherein the infection is a bacterial infection.

Clause 14. The method of clause 12 or clause 13, wherein the bacterial infection is caused by a bacteria selected from the group consisting of *K. pneumoniae, P. aeruginosa, E. coli*, vancomycin-resistant *Enterococcus faecalis*, Methicillin-resistant *S. aureus* (MRSA), and Methicillin-resistant *S. epidermidis* (MRSE).

Clause 15. The method of any one of clauses 12-14, wherein the bacterial infection is caused by MRSA.

Clause 16. The method of any one of clauses 12-15, wherein the bacterial infection is caused by bacteria that form a bacterial biofilm.

Clause 17. The method of clause 16, wherein the bacterial biofilm is formed by MRSA or *E. coli* bacteria.

Clause 18. The method of any one of clauses 12-17, wherein the bacterial infection is resistant to treatment with one or more antibiotics.

Clause 19. The method of any one of clauses 12-18, wherein the compound, or a salt thereof, is administered orally, intravenously, transdermally, or topically.

Clause 20. The method of clause 20, wherein the compound, or a salt thereof, is administered topically.

Clause 21. A method of preventing biofilm formation in a subject in need thereof, the method comprising administering to the subject an effective amount of a compound of any one of clauses 1-10, or a salt thereof.

Clause 22. A method of inhibiting bacterial growth in a subject in need thereof, the method comprising administering to the subject an effective amount of a compound of any one of clauses 1-10, or a salt thereof.

Clause 23. The method of clause 22, wherein the bacterial growth is inhibited by preventing biofilm formation.

What is claimed is:

1. A compound of formula (I), or a salt thereof

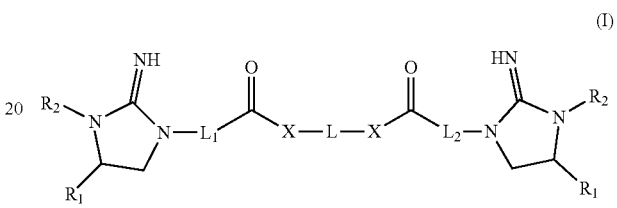

wherein

R$_1$ at each occurrence is independently hydrogen, C$_1$-C$_{10}$ alkyl, alkenyl, alkynyl, aryl, aryl-C$_1$-C$_6$ alkyl, cycloalkyl, or cycloalkyl-C$_1$-C$_6$ alkyl;

R$_2$ at each occurrence is independently hydrogen, C$_1$-C$_{10}$ alkyl, alkenyl, alkynyl, aryl, aryl-C$_1$-C$_6$ alkyl, cycloalkyl, or cycloalkyl-C$_1$-C$_6$ alkyl;

X is O or NH

L$_1$ is —(CR$_x$R$_y$)$_{n1}$;

L$_2$ is —(CR$_x$R$_y$)$_{n2}$;

L is —(CR$_x$R$_y$)$_{n3}$—(CH$_2$CH$_2$O)$_{m1}$-G-(CH$_2$CH$_2$O)$_{m2}$—(CR$_x$R$_y$)$_{n4}$—

R$_x$ and R$_y$ at each occurrence is independently hydrogen or C$_1$-C$_4$ alkyl;

G is a bond or -(G$_1$)$_t$-, wherein G$_1$ at each occurrence is independently aryl, cycloakyl, heteroaryl, or heterocycle;

n1 and n2 are each independently 1-4;

m1, m2, n3, and n4 are each independently 0-10;

t is 1, 2, 3, or 4; and wherein R$_1$, R$_2$, R$_x$, R$_y$, and G$_1$ optionally are each independently substituted with one or more substituents selected from the group consisting of halogen, cyano, —OH, C$_1$-C$_6$ alkoxy, —COOH, C$_1$-C$_6$ alkoxycarbonyl, oxo, and amino.

2. The compound of claim 1, having a structure of formula (I-a)

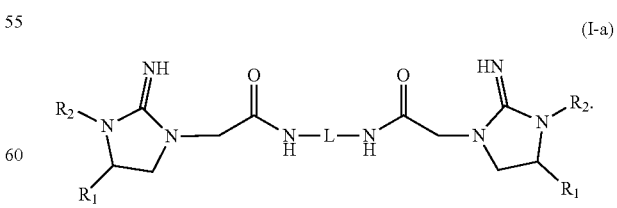

3. The compound of claim 1, wherein L is —(CH$_2$)$_{n3}$— and n3 is 4-8.

4. The compound of claim 1, wherein L is -(G$_1$)$_t$-, and wherein G$_1$ is aryl and t is 1.

5. The compound of claim 4, wherein L is

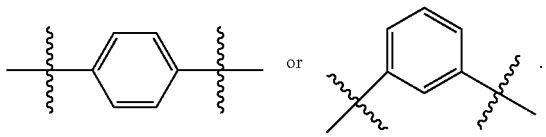 [SMILES: *c1ccc(*)cc1 ; *c1cccc(*)c1]

or

6. The compound of claim 1, wherein $R_1$ is $C_1$-$C_{10}$ alkyl or aryl-$C_1$-$C_6$ alkyl.

7. The compound of claim 1, where in $R_1$ is benzyl.

8. The compound of claim 1, where in $R_2$ is $C_1$-$C_{10}$ alkyl, aryl-$C_1$-$C_6$ alkyl, or cycloalkyl-$C_1$-$C_6$ alkyl.

9. The compound of claim 8, where in $R_2$ is $C_1$-$C_6$ alkyl.

10. The compound of claim 1, wherein $R_1$ is benzyl, $R_2$ is $C_1$-$C_6$ alkyl, and L is

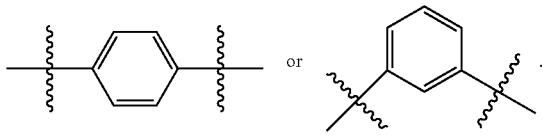

or .

11. A pharmaceutical composition comprising at least one pharmaceutically acceptable carrier and an effective amount of a compound of claim 1.

12. A method of treating infection in a subject in need thereof, the method comprising administering to the subject an effective amount of a compound of claim 1.

13. The method of claim 12, wherein the infection is a bacterial infection.

14. The method of claim 13, wherein the bacterial infection is caused by a bacteria selected from the group consisting of *K. pneumoniae, P. aeruginosa, E. coli*, vancomycin-resistant *Enterococcus faecalis*, Methicillin-resistant *S. aureus* (MRSA), and Methicillin-resistant *S. epidermidis* (MRSE).

15. The method of claim 13, wherein the bacterial infection is caused by MRSA.

16. The method of claim 13, wherein the bacterial infection is caused by bacteria that form a bacterial biofilm.

17. The method of claim 16, wherein the bacterial biofilm is formed by MRSA or *E. coli* bacteria.

18. The method of claim 13, wherein the bacterial infection is resistant to treatment with one or more antibiotics.

19. The method of claim 12, wherein the compound is administered orally, intravenously, transdermally, or topically.

20. The method of claim 19, wherein the compound is administered topically.

* * * * *